(12) United States Patent
Ullrich, Jr. et al.

(10) Patent No.: US 8,551,176 B2
(45) Date of Patent: Oct. 8, 2013

(54) SPINAL IMPLANT HAVING A PASSAGE FOR ENHANCING CONTACT BETWEEN BONE GRAFT MATERIAL AND CORTICAL ENDPLATE BONE

(75) Inventors: Peter F. Ullrich, Jr., Neenah, WI (US); Chad J. Patterson, Port Washington, WI (US)

(73) Assignee: Titan Spine, LLC, Mequon, WI (US)

( * ) Notice: Subject to any disclaimer, the term of this patent is extended or adjusted under 35 U.S.C. 154(b) by 0 days.

(21) Appl. No.: 13/534,624

(22) Filed: Jun. 27, 2012

(65) Prior Publication Data

US 2012/0277876 A1 Nov. 1, 2012

Related U.S. Application Data

(63) Continuation-in-part of application No. 12/151,198, filed on May 5, 2008, now Pat. No. 8,262,737, which is a continuation-in-part of application No. 11/123,359, filed on May 6, 2005, now Pat. No. 7,662,186.

(51) Int. Cl.
*A61F 2/44* (2006.01)

(52) U.S. Cl.
USPC .................... 623/17.16; 623/17.11

(58) Field of Classification Search
USPC .......................... 623/17.11–17.16
See application file for complete search history.

(56) References Cited

U.S. PATENT DOCUMENTS

| | | |
|---|---|---|
| 4,314,876 A | 2/1982 | Kremer et al. |
| 4,904,261 A | 2/1990 | Dove et al. |
| 5,015,247 A | 5/1991 | Michelson |
| 5,071,437 A | 12/1991 | Steffee |
| 5,258,098 A | 11/1993 | Wagner et al. |
| 5,306,308 A | 4/1994 | Gross et al. |
| 5,306,309 A | 4/1994 | Wagner et al. |
| 5,425,772 A | 6/1995 | Brantigan |
| 5,443,514 A | 8/1995 | Steffee |
| 5,456,723 A | 10/1995 | Steinemann et al. |
| 5,507,815 A | 4/1996 | Wagner et al. |
| 5,571,188 A | 11/1996 | Ellingsen et al. |
| 5,603,338 A | 2/1997 | Beaty |

(Continued)

FOREIGN PATENT DOCUMENTS

| | | |
|---|---|---|
| EP | 0599419 | 6/1993 |
| EP | 0916323 | 5/1999 |

(Continued)

OTHER PUBLICATIONS

Astra Tech Dental, "Nanolevel topographic modifications on the OsseoSpeed surface", http://shop.dentsplyimplants.us, Mar. 8, 2001.

(Continued)

*Primary Examiner* — Eduardo C Robert
*Assistant Examiner* — Julianna N Harvey
(74) *Attorney, Agent, or Firm* — Stradley Ronon Stevens & Young, LLP

(57) ABSTRACT

An interbody spinal implant including a body having a top surface, a bottom surface, opposing lateral sides, opposing anterior and posterior portions, and a substantially hollow center in communication with a vertical aperture, which are filled with a bone graft material. The dimensions, shape, and position of the vertical aperture facilitate contact between the bone graft material and vertebral endplate bone to support and enhance bone growth.

23 Claims, 25 Drawing Sheets

(56) References Cited

U.S. PATENT DOCUMENTS

| | | | |
|---|---|---|---|
| 5,609,635 A * | 3/1997 | Michelson | 623/17.16 |
| 5,702,449 A | 12/1997 | McKay | |
| 5,755,798 A | 5/1998 | Papavero et al. | |
| 5,766,252 A | 6/1998 | Henry et al. | |
| 5,776,199 A | 7/1998 | Michelson | |
| 5,860,973 A | 1/1999 | Michelson | |
| 5,863,201 A | 1/1999 | Lazzara et al. | |
| 5,865,845 A | 2/1999 | Thalgott | |
| 5,876,453 A | 3/1999 | Beaty | |
| 5,885,079 A | 3/1999 | Niznick | |
| 5,888,224 A | 3/1999 | Beckers et al. | |
| 5,922,029 A | 7/1999 | Wagner et al. | |
| 5,968,098 A | 10/1999 | Winslow | |
| 5,984,922 A | 11/1999 | McKay | |
| 6,033,582 A | 3/2000 | Lee et al. | |
| 6,039,762 A | 3/2000 | McKay | |
| 6,059,829 A | 5/2000 | Schlapfer et al. | |
| 6,080,158 A | 6/2000 | Lin | |
| 6,086,613 A | 7/2000 | Camino et al. | |
| 6,096,107 A | 8/2000 | Caracostas et al. | |
| 6,123,705 A | 9/2000 | Michelson | |
| 6,143,032 A | 11/2000 | Schafer et al. | |
| 6,176,882 B1 | 1/2001 | Biedermann et al. | |
| 6,183,255 B1 | 2/2001 | Oshida | |
| 6,193,757 B1 | 2/2001 | Foley et al. | |
| 6,193,762 B1 | 2/2001 | Wagner et al. | |
| 6,241,770 B1 | 6/2001 | Michelson | |
| 6,241,771 B1 | 6/2001 | Gresser et al. | |
| 6,245,108 B1 | 6/2001 | Biscup | |
| 6,296,664 B1 | 10/2001 | Middleton | |
| 6,302,914 B1 | 10/2001 | Michelson | |
| 6,342,074 B1 | 1/2002 | Simpson | |
| 6,344,057 B1 * | 2/2002 | Rabbe et al. | 623/17.11 |
| 6,350,283 B1 | 2/2002 | Michelson | |
| 6,375,681 B1 | 4/2002 | Truscott | |
| 6,387,130 B1 | 5/2002 | Stone et al. | |
| 6,395,031 B1 | 5/2002 | Foley et al. | |
| 6,423,095 B1 | 7/2002 | Van Hoeck et al. | |
| 6,432,140 B1 | 8/2002 | Lin | |
| 6,436,102 B1 | 8/2002 | Ralph et al. | |
| 6,447,544 B1 | 9/2002 | Michelson | |
| 6,458,159 B1 | 10/2002 | Thalgott | |
| 6,478,823 B1 | 11/2002 | Michelson | |
| 6,482,233 B1 | 11/2002 | Aebi et al. | |
| 6,485,517 B1 | 11/2002 | Michelson | |
| 6,491,723 B1 | 12/2002 | Beaty | |
| 6,520,993 B2 | 2/2003 | James et al. | |
| 6,558,424 B2 | 5/2003 | Thalgott | |
| 6,569,201 B2 | 5/2003 | Moumene et al. | |
| 6,579,318 B2 | 6/2003 | Varga et al. | |
| 6,592,624 B1 | 7/2003 | Fraser et al. | |
| 6,599,322 B1 | 7/2003 | Amrich et al. | |
| 6,610,089 B1 | 8/2003 | Liu et al. | |
| 6,620,332 B2 | 9/2003 | Amrich | |
| 6,635,086 B2 | 10/2003 | Lin | |
| 6,652,765 B1 | 11/2003 | Beaty | |
| 6,676,703 B2 | 1/2004 | Biscup | |
| 6,702,855 B1 | 3/2004 | Steinemann et al. | |
| 6,719,794 B2 | 4/2004 | Gerber et al. | |
| 6,726,720 B2 | 4/2004 | Ross et al. | |
| 6,730,127 B2 | 5/2004 | Michelson | |
| 6,740,118 B2 | 5/2004 | Eisermann et al. | |
| 6,743,231 B1 | 6/2004 | Gray et al. | |
| 6,758,849 B1 | 7/2004 | Michelson | |
| 6,833,006 B2 | 12/2004 | Foley et al. | |
| 6,890,355 B2 | 5/2005 | Michelson | |
| 6,902,581 B2 | 6/2005 | Walkenhorst et al. | |
| 6,911,249 B2 | 6/2005 | Wagner et al. | |
| 6,923,810 B1 | 8/2005 | Michelson | |
| 6,964,687 B1 | 11/2005 | Bernard et al. | |
| 6,974,480 B2 | 12/2005 | Messerli et al. | |
| 6,981,975 B2 | 1/2006 | Michelson | |
| 7,018,418 B2 | 3/2006 | Amrich et al. | |
| 7,041,137 B2 | 5/2006 | Fulton et al. | |
| 7,044,972 B2 | 5/2006 | Mathys, Jr. et al. | |
| 7,048,870 B1 | 5/2006 | Ellingsen et al. | |
| 7,060,073 B2 | 6/2006 | Frey et al. | |
| 7,066,961 B2 | 6/2006 | Michelson | |
| 7,077,864 B2 | 7/2006 | Byrd, III et al. | |
| 7,087,085 B2 | 8/2006 | Steinemann et al. | |
| 7,112,224 B2 | 9/2006 | Liu et al. | |
| 7,128,760 B2 | 10/2006 | Michelson | |
| 7,137,997 B2 | 11/2006 | Paul | |
| 7,144,428 B2 | 12/2006 | Anitua | |
| 7,166,129 B2 | 1/2007 | Michelson | |
| 7,169,183 B2 | 1/2007 | Liu et al. | |
| D539,934 S | 4/2007 | Blain | |
| 7,201,775 B2 | 4/2007 | Gorensek et al. | |
| D541,940 S | 5/2007 | Blain | |
| 7,220,280 B2 | 5/2007 | Kast et al. | |
| 7,223,289 B2 | 5/2007 | Trieu et al. | |
| 7,226,480 B2 | 6/2007 | Thalgott | |
| 7,238,186 B2 | 7/2007 | Zdeblick et al. | |
| 7,244,275 B2 | 7/2007 | Michelson | |
| 7,250,060 B2 | 7/2007 | Trieu | |
| 7,255,698 B2 | 8/2007 | Michelson | |
| 7,288,093 B2 | 10/2007 | Michelson | |
| 7,311,734 B2 | 12/2007 | Van Hoeck et al. | |
| D564,095 S | 3/2008 | Blain | |
| 7,347,873 B2 | 3/2008 | Paul et al. | |
| D566,276 S | 4/2008 | Blain | |
| 7,368,065 B2 | 5/2008 | Yang et al. | |
| 7,410,501 B2 | 8/2008 | Michelson | |
| 7,501,073 B2 | 3/2009 | Wen et al. | |
| 7,503,933 B2 | 3/2009 | Michelson | |
| 7,517,363 B2 | 4/2009 | Rogers et al. | |
| D599,019 S | 8/2009 | Pimenta et al. | |
| 7,569,074 B2 | 8/2009 | Eisermann et al. | |
| 7,608,107 B2 | 10/2009 | Michelson | |
| 7,615,078 B2 | 11/2009 | White et al. | |
| 7,655,042 B2 | 2/2010 | Foley et al. | |
| 7,662,186 B2 | 2/2010 | Bagga et al. | |
| 7,662,190 B2 | 2/2010 | Steinemann et al. | |
| 7,744,612 B2 | 6/2010 | Blain | |
| 7,846,183 B2 | 12/2010 | Blain | |
| 7,901,462 B2 | 3/2011 | Yang et al. | |
| 7,998,172 B2 | 8/2011 | Blain | |
| 8,062,304 B2 | 11/2011 | Blain et al. | |
| 8,100,955 B2 | 1/2012 | Blain et al. | |
| 8,142,355 B2 | 3/2012 | Blain et al. | |
| 8,172,854 B2 | 5/2012 | Blain et al. | |
| 8,262,737 B2 | 9/2012 | Bagga et al. | |
| 2001/0014826 A1 | 8/2001 | Biedermann et al. | |
| 2001/0016777 A1 | 8/2001 | Biscup | |
| 2001/0039454 A1 | 11/2001 | Ricci et al. | |
| 2001/0047208 A1 | 11/2001 | Michelson | |
| 2002/0049497 A1 | 4/2002 | Mason | |
| 2002/0087212 A1 * | 7/2002 | James et al. | 623/17.11 |
| 2002/0099443 A1 | 7/2002 | Messerli et al. | |
| 2002/0128716 A1 | 9/2002 | Cohen et al. | |
| 2002/0138142 A1 | 9/2002 | Castro et al. | |
| 2002/0161443 A1 * | 10/2002 | Michelson | 623/17.11 |
| 2002/0173854 A1 | 11/2002 | Amrich | |
| 2002/0188294 A1 | 12/2002 | Couture et al. | |
| 2003/0014116 A1 | 1/2003 | Ralph et al. | |
| 2003/0083668 A1 | 5/2003 | Rogers et al. | |
| 2003/0105527 A1 | 6/2003 | Bresina | |
| 2003/0109928 A1 | 6/2003 | Pasquet et al. | |
| 2003/0125739 A1 | 7/2003 | Bagga et al. | |
| 2003/0153975 A1 * | 8/2003 | Byrd et al. | 623/17.11 |
| 2003/0176925 A1 * | 9/2003 | Paponneau | 623/17.16 |
| 2003/0181980 A1 | 9/2003 | Berry et al. | |
| 2003/0181981 A1 | 9/2003 | Lemaire | |
| 2003/0187506 A1 | 10/2003 | Ross et al. | |
| 2003/0191531 A1 * | 10/2003 | Berry et al. | 623/17.11 |
| 2004/0117019 A1 | 6/2004 | Trieu et al. | |
| 2004/0117020 A1 | 6/2004 | Frey et al. | |
| 2004/0122518 A1 | 6/2004 | Rhoda | |
| 2004/0127993 A1 | 7/2004 | Kast et al. | |
| 2004/0153154 A1 | 8/2004 | Dinkelacker | |
| 2004/0153160 A1 | 8/2004 | Carrasco | |
| 2004/0162616 A1 | 8/2004 | Simonton et al. | |
| 2004/0167632 A1 | 8/2004 | Wen et al. | |
| 2004/0210309 A1 | 10/2004 | Denzer et al. | |

| | | |
|---|---|---|
| 2004/0230306 A1 | 11/2004 | Hoeck et al. |
| 2004/0265780 A1 | 12/2004 | Robb et al. |
| 2004/0267367 A1 | 12/2004 | O'Neil |
| 2005/0021150 A1 | 1/2005 | Michelson |
| 2005/0027360 A1 | 2/2005 | Webb et al. |
| 2005/0038512 A1 | 2/2005 | Michelson |
| 2005/0060034 A1 | 3/2005 | Berry et al. |
| 2005/0075734 A1 | 4/2005 | Fulton et al. |
| 2005/0085913 A1 | 4/2005 | Fraser et al. |
| 2005/0131416 A1 | 6/2005 | Jansen et al. |
| 2005/0147942 A1 | 7/2005 | Hall |
| 2005/0159814 A1 | 7/2005 | Karahalios |
| 2005/0251257 A1 | 11/2005 | Mitchell et al. |
| 2006/0041313 A1 | 2/2006 | Allard et al. |
| 2006/0093646 A1 | 5/2006 | Cima et al. |
| 2006/0100705 A1 | 5/2006 | Puno et al. |
| 2006/0149372 A1 | 7/2006 | Paxson et al. |
| 2006/0149376 A1 | 7/2006 | Shimp et al. |
| 2006/0167549 A1 | 7/2006 | Mathys, Jr. et al. |
| 2006/0190079 A1 | 8/2006 | Istephanous et al. |
| 2006/0219661 A1 | 10/2006 | Towse et al. |
| 2006/0235534 A1 | 10/2006 | Gertzman et al. |
| 2006/0265065 A1 | 11/2006 | Bagga et al. |
| 2006/0293748 A1 | 12/2006 | Alexander et al. |
| 2007/0010885 A1 | 1/2007 | Liu et al. |
| 2007/0093898 A1 | 4/2007 | Schwab et al. |
| 2007/0118220 A1 | 5/2007 | Liu et al. |
| 2007/0118223 A1 | 5/2007 | Allard et al. |
| 2007/0233247 A1 | 10/2007 | Schwab |
| 2007/0233248 A1 | 10/2007 | Schwab et al. |
| 2007/0260320 A1 | 11/2007 | Peterman et al. |
| 2007/0270951 A1 | 11/2007 | Davis et al. |
| 2007/0270956 A1 | 11/2007 | Heinz |
| 2007/0282441 A1 | 12/2007 | Stream et al. |
| 2007/0288028 A1 | 12/2007 | Gorensek et al. |
| 2007/0293949 A1 | 12/2007 | Salerni et al. |
| 2008/0004705 A1* | 1/2008 | Rogeau et al. ............. 623/17.16 |
| 2008/0014243 A1 | 1/2008 | Ellingsen et al. |
| 2008/0071380 A1 | 3/2008 | Sweeney |
| 2008/0077171 A1 | 3/2008 | Blain et al. |
| 2008/0154378 A1 | 6/2008 | Pelo |
| 2008/0195209 A1 | 8/2008 | Garcia et al. |
| 2008/0221689 A1 | 9/2008 | Chaput et al. |
| 2008/0249622 A1 | 10/2008 | Gray |
| 2008/0262623 A1 | 10/2008 | Bagga et al. |
| 2008/0269764 A1 | 10/2008 | Blain et al. |
| 2008/0269806 A1 | 10/2008 | Zhang et al. |
| 2009/0005784 A1 | 1/2009 | Blain et al. |
| 2009/0014243 A1 | 1/2009 | Whigham |
| 2009/0024132 A1 | 1/2009 | Blain et al. |
| 2009/0082819 A1 | 3/2009 | Blain et al. |
| 2009/0088800 A1 | 4/2009 | Blain et al. |
| 2009/0088853 A1 | 4/2009 | Ogilvie et al. |
| 2009/0132048 A1 | 5/2009 | Denzer |
| 2009/0182432 A1 | 7/2009 | Zdeblick et al. |
| 2009/0187247 A1 | 7/2009 | Metcalf, Jr. et al. |
| 2009/0204152 A1 | 8/2009 | Blain |
| 2009/0234362 A1 | 9/2009 | Blain et al. |
| 2009/0264928 A1 | 10/2009 | Blain |
| 2009/0276049 A1 | 11/2009 | Weiland |
| 2009/0312837 A1 | 12/2009 | Eisermann et al. |
| 2010/0121385 A1 | 5/2010 | Blain et al. |
| 2010/0173264 A1 | 7/2010 | Fredriksson et al. |
| 2010/0204798 A1 | 8/2010 | Gerbec et al. |
| 2010/0218854 A1 | 9/2010 | Garcia Saban et al. |
| 2010/0228288 A1 | 9/2010 | Blain |
| 2010/0249937 A1 | 9/2010 | Blain et al. |
| 2010/0274286 A1 | 10/2010 | Blain et al. |
| 2011/0040301 A1 | 2/2011 | Blain et al. |
| 2011/0082503 A1 | 4/2011 | Blain |
| 2011/0224796 A1 | 9/2011 | Weiland et al. |
| 2011/0230970 A1 | 9/2011 | Lynn et al. |
| 2011/0233169 A1 | 9/2011 | Mayfield et al. |
| 2011/0282454 A1 | 11/2011 | Ullrich, Jr. et al. |
| 2012/0009341 A1 | 1/2012 | Noh et al. |
| 2012/0046695 A9 | 2/2012 | Blain |
| 2012/0123424 A1 | 5/2012 | Blain et al. |
| 2012/0123548 A1 | 5/2012 | Lynn et al. |
| 2012/0136443 A1 | 5/2012 | Wentzel |
| 2012/0149991 A1 | 6/2012 | Blain et al. |
| 2012/0158056 A1 | 6/2012 | Blain |
| 2012/0158144 A1 | 6/2012 | Ullrich, Jr. et al. |
| 2012/0172991 A1 | 7/2012 | Bertele et al. |
| 2012/0232664 A1 | 9/2012 | Ulrich, Jr. et al. |
| 2012/0239150 A1 | 9/2012 | Ullrich, Jr. et al. |
| 2012/0239151 A1 | 9/2012 | Ulrich, Jr. et al. |
| 2012/0239152 A1 | 9/2012 | Ullrich, Jr. et al. |
| 2012/0239153 A1 | 9/2012 | Ullrich, Jr. et al. |
| 2012/0239154 A1 | 9/2012 | Ullrich, Jr. et al. |
| 2012/0245694 A1 | 9/2012 | Ullrich, Jr. et al. |
| 2012/0277876 A1 | 11/2012 | Ullrich, Jr. et al. |
| 2012/0303127 A1 | 11/2012 | Ullrich, Jr. et al. |
| 2012/0303128 A1 | 11/2012 | Ullrich, Jr. et al. |
| 2012/0303129 A1 | 11/2012 | Bagga et al. |
| 2012/0310354 A1 | 12/2012 | Ullrich, Jr. et al. |
| 2012/0312778 A1 | 12/2012 | Ullrich, Jr. et al. |
| 2012/0312779 A1 | 12/2012 | Patterson et al. |
| 2012/0316650 A1 | 12/2012 | Ullrich, Jr. et al. |
| 2012/0316651 A1 | 12/2012 | Ullrich, Jr. et al. |
| 2012/0316653 A1 | 12/2012 | Ullrich, Jr. et al. |
| 2013/0006363 A1 | 1/2013 | Ullrich, Jr. et al. |

FOREIGN PATENT DOCUMENTS

| | | |
|---|---|---|
| EP | 1449544 | 8/2004 |
| EP | 2 386 274 A1 | 11/2011 |
| JP | 08010276 | 1/1996 |
| JP | 19968010276 | 1/1996 |
| JP | 2001170092 | 6/2001 |
| WO | 9706753 | 2/1997 |
| WO | 98/01091 | 1/1998 |
| WO | 0128469 | 4/2001 |
| WO | 0170144 | 9/2001 |
| WO | 0195838 | 12/2001 |
| WO | 2004041131 | 5/2004 |
| WO | 2006081843 | 8/2006 |
| WO | 2006116306 | 11/2006 |
| WO | 2006119088 | 11/2006 |
| WO | 2006121795 | 11/2006 |
| WO | 2007089905 | 8/2007 |
| WO | 2008103843 | 8/2008 |
| WO | 2009006225 | 1/2009 |
| WO | 2009029458 | 3/2009 |
| WO | 2009129262 | 10/2009 |
| WO | 2009140544 | 11/2009 |

OTHER PUBLICATIONS

Astra Tech Dental, "OsseoSpeed—more bone more rapidly", http://shop.dentsplyimplants.us, May 2011.

Guo, et al., "The effect of hydrofluoric acid treatment of TiO2 grit blasted titanium implants on adherent osteoblast gene expression in vitro and in vivo", Biomaterials 28 (Sep. 14, 2007) 5418-5425.

He, et al., "Mechanical and Histomorphometric Evaluations of Rough Titanium Implants Treated with Hydrofluoric Acid/Nitric Acid Solution in Rabbit Tibia", Int. J. Oral Maxillofac. Implants, Nov. 1, 2011; 26:115-122.

Isa, et al., "Effects of Fluoride-Modified Titanium Surfaces on Osteoblast Proliferation and Gene Expression", Int. J. Oral Maxillofac. Implants 2006; 21:203-211.

Lamolle, et al., "The effect of hydrofluoric acid treatment of titanium surface on nanostructural and chemical changes and the growth of MC3T3-E1 cells", Biomaterials 30 (Nov. 20, 2008) 736-742.

Meirelles, et al., "The Effect of Chemical and Nanotopographical Modifications on the Early Stages of Osseointegration", Int. J. Oral Maxillofac. Implants 2008; 23:641-647.

Supplementary Partial European Search Report issued Sep. 27, 2011, for EP 06 75 9086.

Supplementary Partial European Search Report issued Aug. 19, 2011, for EP 06 75 9086.

Variola, et al., "Nanoscale surface modifications of medically relevant metals: state-of-the art and prespectives", Nanoscale, 2011, 3, 335-353.

Wennerberg, et al., "Spontaneously formed nanostructures on titanium surfaces", Clin. Oral Impl. Res., 2012, 1-7.

Wennerberg, A., et al., "Effects of titanium surface topography on bone integration: a systematic review", Clin. Oral Impl. Res., 20 (Suppl. 4), 2009, pp. 172-184.

Pending U.S. Appl. No. 13/286,813 of Chad J. Patterson, et al. filed Nov. 1, 2011.

Pending U.S. Appl. No. 13/826,304 of Peter F. Ullrich, Jr., et al. filed Mar. 14, 2013.

Pending U.S. Appl. No. 13/713,417 of Chad J. Patterson, et al. filed Dec. 13, 2012.

Pending U.S. Appl. No. 13/784,144 of Peter F. Ullrich, Jr., et al. filed Mar. 4, 2013.

* cited by examiner

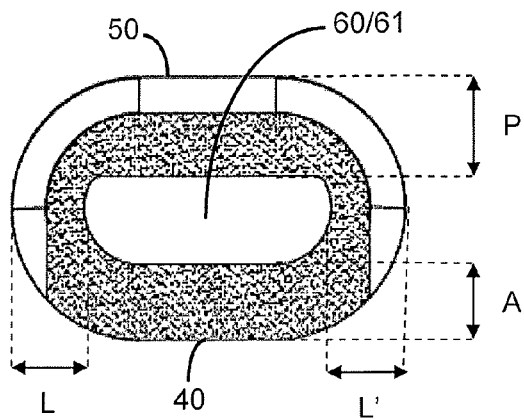
FIG. 16A
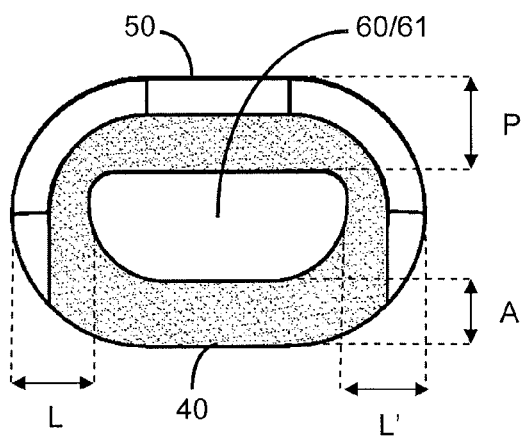
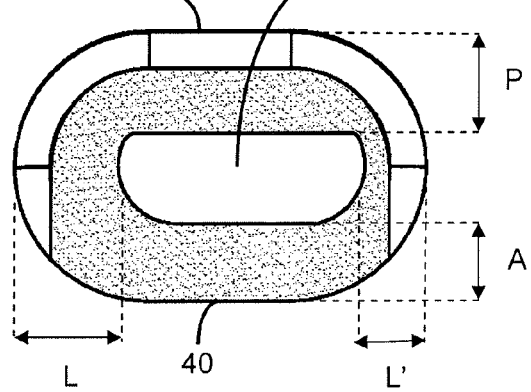
FIG. 16B
FIG. 16C
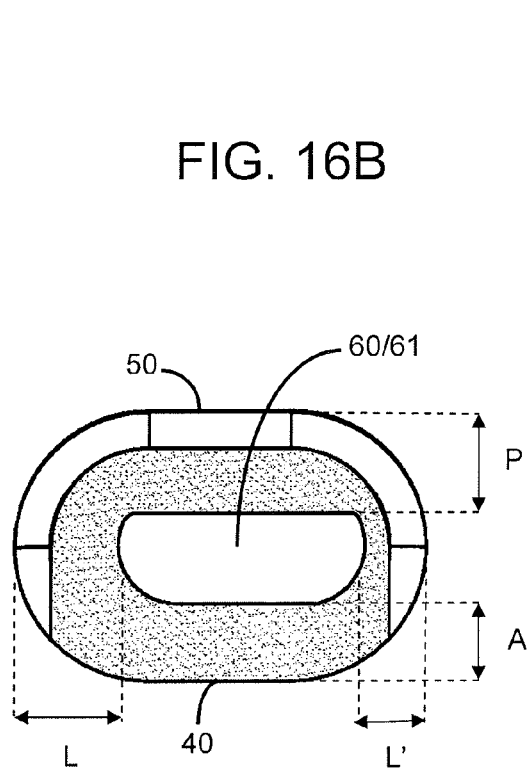
FIG. 16D
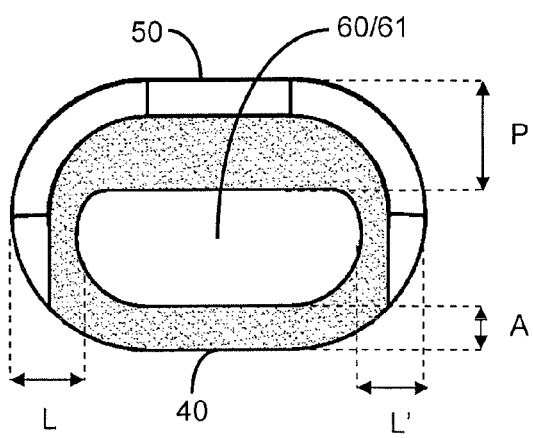

SPINAL IMPLANT HAVING A PASSAGE FOR ENHANCING CONTACT BETWEEN BONE GRAFT MATERIAL AND CORTICAL ENDPLATE BONE

CROSS REFERENCE TO RELATED APPLICATIONS

This application is a continuation-in-part of U.S. patent application Ser. No. 12/151,198, filed on May 5, 2008, and pending, which is a continuation-in-part of U.S. patent application Ser. No. 11/123,359, filed on May 6, 2005, and issued as U.S. Pat. No. 7,662,186. The contents of both prior applications are incorporated by reference in this document, in their entirety and for all purposes.

FIELD OF THE INVENTION

The invention relates generally to interbody spinal implants and methods of using such implants and, more particularly, to an implant including an anti-expulsion edge on one or more of its anterior, posterior or lateral portions. The anti-expulsion edge may be comprised on the top and/or bottom surface of the implant body itself, or on the top surface of one or more integration plates affixed to the implant body.

BACKGROUND OF THE INVENTION

In the simplest terms, the spine is a column made of vertebrae and discs. The vertebrae provide the support and structure of the spine while the spinal discs, located between the vertebrae, act as cushions or "shock absorbers." These discs also contribute to the flexibility and motion of the spinal column. Over time, the discs may become diseased or infected, may develop deformities such as tears or cracks, or may simply lose structural integrity (e.g., the discs may bulge or flatten). Impaired discs can affect the anatomical functions of the vertebrae, due to the resultant lack of proper biomechanical support, and are often associated with chronic back pain.

Several surgical techniques have been developed to address spinal defects, such as disc degeneration and deformity. Spinal fusion has become a recognized surgical procedure for mitigating back pain by restoring biomechanical and anatomical integrity to the spine. Spinal fusion techniques involve the removal, or partial removal, of at least one intervertebral disc and preparation of the disc space for receiving an implant by shaping the exposed vertebral endplates. An implant is then inserted between the opposing endplates.

Several interbody implant systems have been introduced to facilitate interbody fusion. Traditional threaded implants involve at least two cylindrical bodies, each typically packed with bone graft material, surgically placed on opposite sides of the mid-sagittal plane through pre-tapped holes within the intervertebral disc space. This location is not the preferable seating position for an implant system, however, because only a relatively small portion of the vertebral endplate is contacted by these cylindrical implants. Accordingly, these implant bodies will likely contact the softer cancellous bone rather than the stronger cortical bone, or apophyseal rim, of the vertebral endplate. The seating of these threaded cylindrical implants may also compromise biomechanical integrity by reducing the area in which to distribute mechanical forces, thus increasing the apparent stress experienced by both the implant and vertebrae. Still further, a substantial risk of implant subsidence (defined as sinking or settling) into the softer cancellous bone of the vertebral body may arise from such improper seating.

In contrast, open ring-shaped cage implant systems are generally shaped to mimic the anatomical contour of the vertebral body. Traditional ring-shaped cages are generally comprised of allograft bone material, however, harvested from the human femur. Such allograft bone material restricts the usable size and shape of the resultant implant. For example, many of these femoral ring-shaped cages generally have a medial-lateral width of less than 25 mm. Therefore, these cages may not be of a sufficient size to contact the strong cortical bone, or apophyseal rim, of the vertebral endplate. These size-limited implant systems may also poorly accommodate related instrumentation such as drivers, reamers, distractors, and the like. For example, these implant systems may lack sufficient structural integrity to withstand repeated impact and may fracture during implantation. Still further, other traditional non-allograft ring-shaped cage systems may be size-limited due to varied and complex supplemental implant instrumentation which may obstruct the disc space while requiring greater exposure of the operating space. These supplemental implant instrumentation systems also generally increase the instrument load upon the surgeon.

The surgical procedure corresponding to an implant system should preserve as much vertebral endplate bone surface as possible by minimizing the amount of bone removed. This vertebral endplate bone surface, or subchondral bone, is generally much stronger than the underlying cancellous bone. Preservation of the endplate bone stock ensures biomechanical integrity of the endplates and minimizes the risk of implant subsidence. Thus, proper interbody implant design should provide for optimal seating of the implant while utilizing the maximum amount of available supporting vertebral bone stock.

Nevertheless, traditional implantation practices often do not preserve critical bone structures such as vertebral endplates during the surgical procedure. In some cases, the implant devices themselves necessitate removal of bone and were not designed or implanted with the intent to preserve critical bone structures during or after implantation.

In summary, at least ten, separate challenges can be identified as inherent in traditional anterior spinal fusion devices. Such challenges include: (1) end-plate preparation; (2) implant difficulty; (3) materials of construction; (4) implant expulsion; (5) implant subsidence; (6) insufficient room for bone graft; (7) stress shielding; (8) lack of implant incorporation with vertebral bone; (9) limitations on radiographic visualization; and (10) cost of manufacture and inventory.

SUMMARY OF THE INVENTION

The invention is directed to interbody spinal implants and to methods of using such implants. The implants can be inserted, using methods of the invention, from a variety of vantages, including anterior, antero-lateral, and lateral implantation. The spinal implant is preferably adapted to be inserted into a prepared disc space via a procedure which does not destroy the vertebral end-plates, or contacts the vertebral end-plates only peripherally, allowing the intact vertebral end-plates to deflect like a diaphragm under axial compressive loads generated due to physiologic activities and pressurize the bone graft material disposed inside the spinal implant.

An implant preferably comprises a body having a top surface, a bottom surface, opposing lateral sides, opposing anterior and posterior portions, a substantially hollow center, and a single vertical aperture extending from the top surface to the bottom surface.

The vertical aperture has a size and shape for maximizing the surface area of the top surface and the bottom surface available for contacting vertebral endplate bone and maximizing the contact of a bone graft material with vertebral endplate bone, when a bone graft material is disposed in the substantially hollow center and extends into the aperture such that it may make contact with the vertebral endplate bone. The vertical aperture defines a transverse rim on the top surface and on the bottom surface, and this transverse rim comprises an anterior portion width, a posterior portion width, a first lateral side width, and a second lateral side width. The vertical aperture comprises a maximum width at its center, the size of this width ranges from about 40% to about 80% of the distance (e.g., width) between the edges of the opposing lateral sides.

In some embodiments, the anterior portion width of the transverse rim is less than the posterior portion width of the rim. In some embodiments, the posterior portion width of the transverse rim is less than the anterior portion width of the rim. In some embodiments, the first lateral side width of the transverse rim is less than the second lateral side width of the rim.

An implant preferably comprises a body and at least one integration plate, which are joined together. An implant preferably comprises a body having a top surface, a bottom surface, opposing lateral sides, opposing anterior and posterior portions, a substantially hollow center, and a single vertical aperture extending from the top surface to the bottom surface.

Each integration plate comprises a top surface, a bottom surface, opposing lateral sides, opposing anterior and posterior portions, and a single vertical aperture extending from the top surface to the bottom surface. Preferably, the vertical aperture aligns with the single vertical aperture of the body. The vertical aperture of the integration plate has a size and shape for maximizing the surface area of the top surface and the bottom surface of the integration plate available for contacting vertebral endplate bone and maximizing the contact of a bone graft material with vertebral endplate bone, when a bone graft material is disposed in the substantially hollow center and extends into the aperture such that it may make contact with the vertebral endplate bone. The vertical aperture defines a transverse rim on the top surface of the integration plate, and this transverse rim comprises an anterior portion width, a posterior portion width, a first lateral side width, and a second lateral side width. The vertical aperture comprises a maximum width at its center, the size of this width ranges from about 40% to about 80% of the distance (e.g., width) between the edges of the opposing lateral sides of the integration plate, or between the edges of the opposing lateral sides of the implant body, to the extent the sides of the body extend further than the sides of the integration plate.

In some embodiments, the anterior portion width of the integration plate transverse rim is less than the posterior portion width of the rim. In some embodiments, the posterior portion width of the integration plate transverse rim is less than the anterior portion width of the rim. In some embodiments, the first lateral side width of the integration plate transverse rim is less than the second lateral side width of the rim.

The top surface of the body or of the integration plate preferably comprises a roughened surface topography adapted to grip bone and inhibit migration of the implant. The top surface of the body or the integration plate may comprise an anti-expulsion edge that protrudes above the horizontal plane and also aids in inhibiting migration of the implant The substantially hollow portion of the body and the vertical aperture of the body and the vertical aperture of the integration plate may contain a bone graft material adapted to facilitate the formation of a solid fusion column within the spine. The bone graft material may be cancellous autograft bone, allograft bone, demineralized bone matrix (DBM), porous synthetic bone graft substitute, bone morphogenic protein (BMP), or a combination thereof. The body may comprise a wall closing at least one of the opposing anterior and posterior portions of the body for containing the bone graft material.

The implant body and/or the integration plate may be fabricated from a metal. A preferred metal is titanium. The implant body may be fabricated from a non-metallic material, non-limiting examples of which include polyetherether-ketone, hedrocel, ultra-high molecular weight polyethylene, and combinations thereof. The implant body may be fabricated from both a metal and a non-metallic material, including a composite thereof. For example, a composite may be formed, in part, of titanium and, in part, of polyetherether-ketone, hedrocel, ultra-high molecular weight polyethylene, or combinations thereof.

The body and the integration plate are preferably compatibly shaped, such that the implant with the body and integration plate joined together may have a generally oval shape, a generally rectangular shape, a generally curved shape, or any other shape described or exemplified in this specification. Thus, for example, the body and the integration plate may be generally oval-shaped in transverse cross-section. The body and the integration plate may be generally rectangular-shaped in transverse cross-section. The body and the integration plate may be generally curved-shaped in transverse cross-section.

It is to be understood that both the foregoing general description and the following detailed description are exemplary, but are not restrictive, of the invention.

BRIEF DESCRIPTION OF THE DRAWINGS

The invention is best understood from the following detailed description when read in connection with the accompanying drawing. It is emphasized that, according to common practice, the various features of the drawing are not to scale. On the contrary, the dimensions of the various features are arbitrarily expanded or reduced for clarity. Included in the drawing are the following figures:

FIG. 16A shows a top view of an embodiment of a vertical aperture for the implant of FIG. 15;

FIG. 16B shows a top view of another embodiment of a vertical aperture for the implant of FIG. 15;

FIG. 16C shows a top view of another embodiment of a vertical aperture for the implant of FIG. 15;

FIG. 16D shows a top view of another embodiment of a vertical aperture for the implant of FIG. 15;

DETAILED DESCRIPTION OF THE INVENTION

Certain embodiments of the invention may be especially suited for placement between adjacent human vertebral bodies. The implants of the invention may be used in procedures such as Anterior Lumbar Interbody Fusion (ALIF), Posterior Lumbar Interbody Fusion (PLIF), Transforaminal Lumbar Interbody Fusion (TLIF), and cervical fusion. Certain embodiments do not extend beyond the outer dimensions of the vertebral bodies.

The ability to achieve spinal fusion is directly related to the available vascular contact area over which fusion is desired, the quality and quantity of the fusion mass, and the stability of the interbody spinal implant. Interbody spinal implants, as now taught, allow for improved seating over the apophyseal rim of the vertebral body. Still further, interbody spinal implants, as now taught, better utilize this vital surface area over which fusion may occur and may better bear the considerable biomechanical loads presented through the spinal column with minimal interference with other anatomical or neurological spinal structures. Even further, interbody spinal implants, according to certain aspects of the invention, allow for improved visualization of implant seating and fusion assessment. Interbody spinal implants, as now taught, may also facilitate osteointegration with the surrounding living bone.

Anterior interbody spinal implants in accordance with certain aspects of the invention can be preferably made of a durable material such as stainless steel, stainless steel alloy, titanium, or titanium alloy, but can also be made of other durable materials such as, but not limited to, polymeric, ceramic, and composite materials. For example, certain embodiments of the invention may be comprised of a biocompatible, polymeric matrix reinforced with bioactive fillers, fibers, or both. Certain embodiments of the invention may be comprised of urethane dimethacrylate (DUDMA)/tri-ethylene glycol dimethacrylate (TEDGMA) blended resin and a plurality of fillers and fibers including bioactive fillers and E-glass fibers. Durable materials may also consist of any number of pure metals, metal alloys, or both. Titanium and its alloys are generally preferred for certain embodiments of the invention due to their acceptable, and desirable, strength and biocompatibility. In this manner, certain embodiments of the present interbody spinal implant may have improved structural integrity and may better resist fracture during implantation by impact. Interbody spinal implants, as now taught, may therefore be used as a distractor during implantation.

Figure 1A:
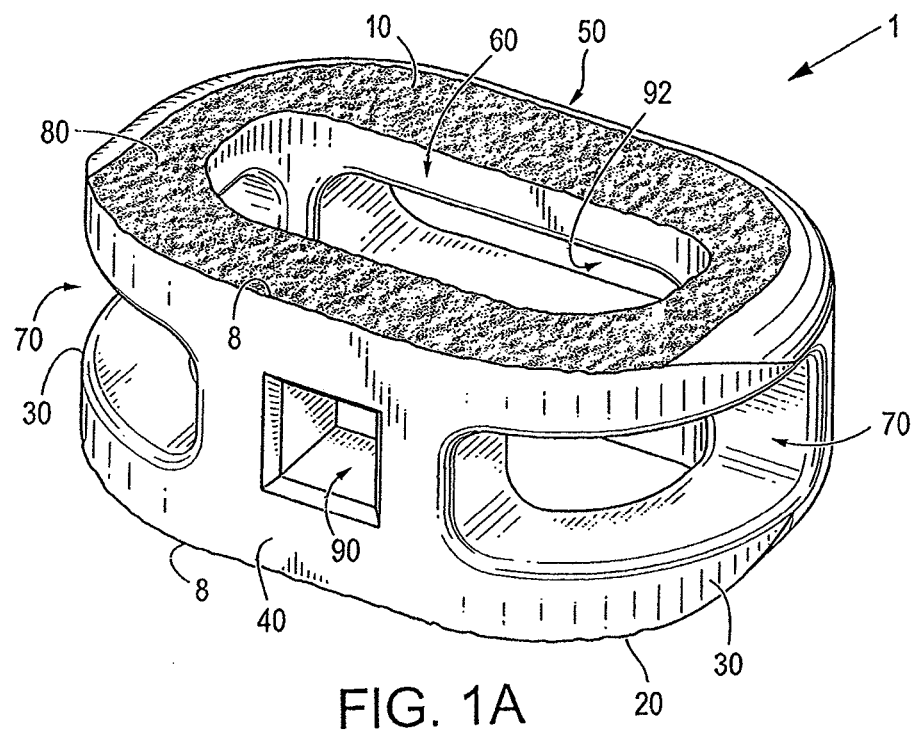
FIG. 1A shows a perspective view of an embodiment of the interbody spinal implant having a generally oval shape and roughened surface topography on the top surface.
Figure 1B:
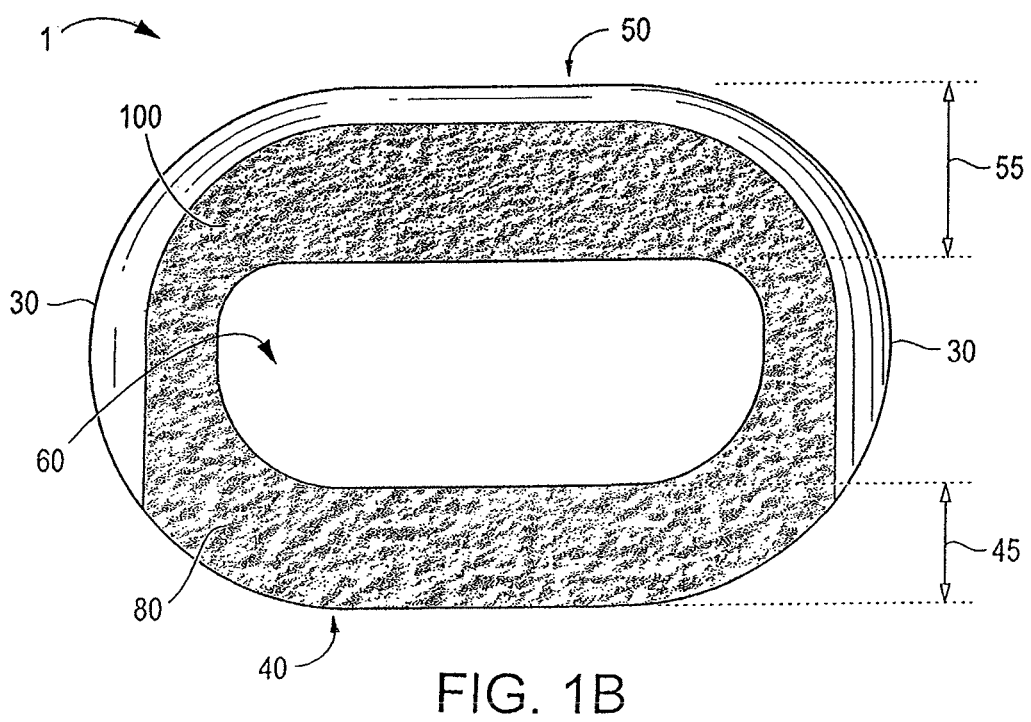
FIG. 1B shows a top view of the first embodiment of the interbody spinal implant illustrated in FIG. 1A.

Referring now to the drawing, in which like reference numbers refer to like elements throughout the various figures that comprise the drawing, FIG. 1 shows a perspective view of a first embodiment of the interbody spinal implant 1 especially well adapted for use in an ALIF procedure.

The interbody spinal implant 1 includes a body having a top surface 10, a bottom surface 20, opposing lateral sides 30, and opposing anterior 40 and posterior 50 portions. One or both of the top surface 10 and the bottom surface 20 has a roughened topography 80. The roughened topography 80, however, is distinct from the teeth provided on the surfaces of some conventional devices.

In some aspects, the interbody spinal implant 1 is substantially hollow and has a generally oval-shaped transverse cross-sectional area with smooth, rounded, or both smooth and rounded lateral sides 30 and posterior-lateral corners 52. A substantially hollow implant 1 includes an implant 1 having at least about 33% of the interior volume of the implant 1 vacant. The implant 1 includes at least one vertical aperture 60 that extends the entire height of the implant body.

It is generally believed that the surface of an implant determines its ultimate ability to integrate into the surrounding living bone. Without being limited to any particular theory or mechanism of action, it is believed that the cumulative effects of at least implant composition, implant surface energy, and implant surface roughness play a major role in the biological response to, and osteointegration of, an implant device. Thus, implant fixation may depend, at least in part, on the attachment and proliferation of osteoblasts and like-functioning cells upon the implant surface.

It is believed that cells attach more readily to relatively rough surfaces rather than smooth surfaces. In this manner, a surface may be bioactive due to its ability to facilitate cellular attachment and osteointegration. The surface roughened topography 80 may better promote the osteointegration of the implant 1. The surface roughened topography 80 may also better grip the vertebral endplate surfaces and inhibit implant migration of the implant 1 upon placement and seating in a patient.

Accordingly, the implant 1 further includes the roughened topography 80 on at least a portion of its top 10 and bottom 20 surfaces for gripping adjacent bone and inhibiting migration of the implant 1. FIG. 1 shows roughened topography 80 on an embodiment of the implant 1.

The roughened topography 80 may be obtained through a variety of techniques including, without limitation, chemical etching, shot peening, plasma etching, laser etching, or abrasive blasting (such as sand or grit blasting). In at least one embodiment, the interbody spinal implant 1 may be comprised of titanium, or a titanium alloy, having the surface roughened topography 80. The surfaces of the implant 1 are preferably bioactive.

In a preferred embodiment of the invention, the roughened topography 80 is obtained via the repetitive masking and chemical or electrochemical milling processes described in U.S. Pat. No. 5,258,098; No. 5,507,815; No. 5,922,029; and No. 6,193,762. Each of these patents is incorporated in this document by reference. Where the invention employs chemical etching, the surface is prepared through an etching process which utilizes the random application of a maskant and subsequent etching of the metallic substrate in areas unprotected by the maskant. This etching process is repeated a number of times as necessitated by the amount and nature of the irregularities required for any particular application. Control of the strength of the etchant material, the temperature at which the etching process takes place, and the time allotted for the etching process allow fine control over the resulting surface produced by the process. The number of repetitions of the etching process can also be used to control the surface features.

By way of example, an etchant mixture of nitric acid ($HNO_3$) and hydrofluoric (HF) acid may be repeatedly applied to a titanium surface to produce an average etch depth of about 0.53 mm. Interbody spinal implants 1, in accordance with some preferred embodiments of the invention, may be comprised of titanium, or a titanium alloy, having an average surface roughness of about 100 µm. Surface roughness may be measured using a laser profilometer or other standard instrumentation.

In another example, chemical modification of the titanium implant surfaces can be achieved using HF and a combination of hydrochloric acid and sulfuric acid ($HCl/H_2SO_4$). In a dual acid etching process, the first exposure is to HF and the second is to $HCl/H_2SO_4$. Chemical acid etching alone of the titanium implant surface has the potential to greatly enhance osteointegration without adding particulate matter (e.g., hydroxyapatite) or embedding surface contaminants (e.g., grit particles) and this surface can be bioactive, for example, by inducing or supporting bone formation by cellular reactions.

The implant 1 may be shaped to reduce the risk of subsidence, and improve stability, by maximizing contact with the apophyseal rim of vertebral endplates. Embodiments may be provided in a variety of anatomical footprints having a medial-lateral width ranging from about 32 mm to about 44 mm. An interbody spinal implant 1 generally does not require extensive supplemental or obstructive implant instrumentation to maintain the prepared disc space during implantation. Thus, the interbody spinal implant 1 and associated implantation methods allow for larger-sized implants as compared with other size-limited interbody spinal implants known in the art. This advantage allows for greater medial-lateral width and correspondingly greater contact with the apophyseal rim. The implant 1 may also include an anti-expulsion edge 8 as described in more detail below.

As illustrated in FIG. 1, the implant 1 has an opening 90 in the anterior portion 40. In one embodiment the posterior portion 50 has a similarly shaped opening 90. In some aspects, only the anterior portion 40 has the opening 90 while the posterior portion 50 has an alternative opening 92 (which may have a size and shape different from the opening 90).

The opening 90 has a number of functions. One function is to facilitate manipulation of the implant 1 by the caretaker. Thus, the caretaker may insert a surgical tool into the opening 90 and, through the engagement between the surgical tool and the opening 90, manipulate the implant 1. The opening 90 may be threaded to enhance the engagement.

The implant 1 may further include at least one transverse aperture 70 that extends the entire transverse length of the implant body. The at least one transverse aperture 70 may provide improved visibility of the implant 1 during surgical procedures to ensure proper implant placement and seating, and may also improve post-operative assessment of implant fusion. Still further, the substantially hollow area defined by the implant 1 may be filled with cancellous autograft bone, allograft bone, DBM, porous synthetic bone graft substitute, BMP, or combinations of these materials (collectively, bone graft materials), to facilitate the formation of a solid fusion column within the spine of a patient.

Certain embodiments of the invention are particularly suited for use during interbody spinal implant procedures (or vertebral body replacement procedures) and may act as a final distractor during implantation, thus minimizing the instrument load upon the surgeon. For example, in such a surgical procedure, the spine may first be exposed via an anterior approach and the center of the disc space identified. The disc space is then initially prepared for implant insertion by removing vertebral cartilage. Soft tissue and residual cartilage may then also be removed from the vertebral endplates.

Vertebral distraction may be performed using trials of various-sized embodiments of the interbody spinal implant 1. The determinatively sized interbody implant 1 may then be inserted in the prepared disc space for final placement. The distraction procedure and final insertion may also be performed under fluoroscopic guidance. The substantially hollow area within the implant body may optionally be filled, at least partially, with bone fusion-enabling materials such as, without limitation, cancellous autograft bone, allograft bone, DBM, porous synthetic bone graft substitute, BMP, or combinations of those materials. Such bone fusion-enabling material may be delivered to the interior of the interbody spinal implant 1 using a delivery device mated with the opening 90 in the anterior portion 40 of the implant 1. The interbody spinal implant 1 may be generally larger than those currently known in the art, and therefore have a correspondingly larger hollow area which may deliver larger volumes of fusion-enabling bone graft material. The bone graft material may be delivered such that it fills the full volume, or less than the full volume, of the implant interior and surrounding disc space appropriately.

Figure 2:
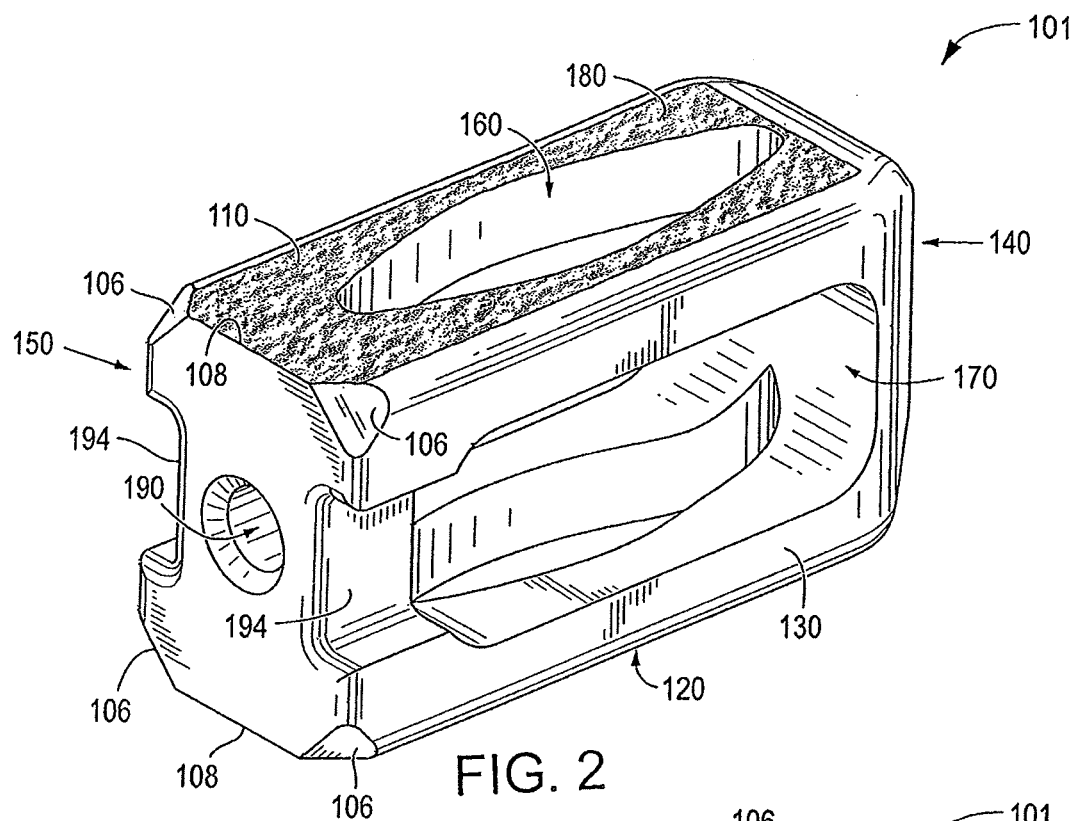
FIG. 2 shows a perspective view from the front of another embodiment of the interbody spinal implant according to the invention.
Figure 3:
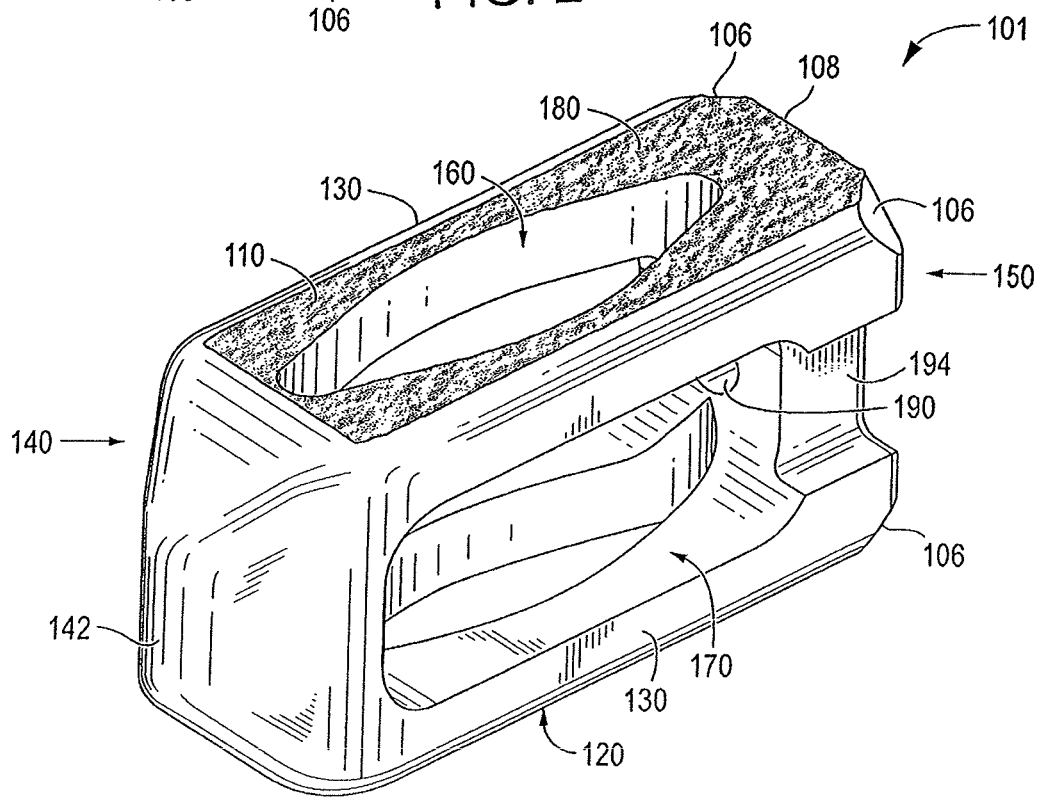
FIG. 3 shows a perspective view from the rear of the embodiment of the interbody spinal implant illustrated in FIG. 2.

As noted above, FIG. 1 shows a perspective view of one embodiment of the invention, the interbody spinal implant 1, which is especially well adapted for use in an ALIF procedure. Other embodiments of the invention are better suited for PLIF, TLIF, or cervical fusion procedures. Specifically, FIGS. 2 and 3 show perspective views, from the front and rear, respectively, of an embodiment of an interbody spinal implant 101 especially well adapted for use in a PLIF procedure. The interbody spinal implant 101 includes a body having a top surface 110, a bottom surface 120, opposing lateral sides 130, and opposing anterior 140 and posterior 150 portions. One or both of the top surface 110 and the bottom surface 120 has a roughened topography 180 for gripping adjacent bone and inhibiting migration of the implant 101.

Certain embodiments of the interbody spinal implant 101 are substantially hollow and have a generally rectangular shape with smooth, rounded, or both smooth and rounded lateral sides and anterior-lateral corners. As best shown in FIG. 3, the anterior portion 140 may have a tapered nose 142 to facilitate insertion of the implant 101. To further facilitate insertion, the implant 101 has chamfers 106 at the corners of its posterior portion 150. The chamfers 106 prevent the implant 101 from catching upon insertion, risking potential damage such as severed nerves, while still permitting the implant 101 to have an anti-expulsion edge 108.

The implant 101 includes at least one vertical aperture 160 that extends the entire height of the implant body. The vertical aperture 160 further defines a transverse rim 200.

As illustrated in FIG. 2, the implant 101 has an opening 190 in the posterior portion 150. The opening 190 has a number of functions. One function is to facilitate manipulation of the implant 101 by the caretaker. Thus, the caretaker may insert a surgical tool into the opening 190 and, through the engagement between the surgical tool and the opening 190, manipulate the implant 101. The opening 190 may be threaded to enhance the engagement.

The implant 101 may also have an Implant Holding Feature (IHF) 194 instead of or in addition to the opening 190. As illustrated in FIG. 2, the IHF 194 is located proximate the opening 190 in the posterior portion 150. In this particular example, the IHF 194 is a U-shaped notch. Like the opening 190, the IHF 194 has a number of functions, one of which is to facilitate manipulation of the implant 101 by the caretaker. Other functions of the opening 190 and the IHF 194 are to increase visibility of the implant 101 during surgical procedures and to enhance engagement between bone graft material and adjacent bone.

The implant 101 may further include at least one transverse aperture 170. Like the vertical aperture 160, the size and shape of the transverse aperture 170 are carefully chosen (and predetermined) to achieve a preferable design tradeoff for the particular application envisioned for the implant 101. Specifically, the transverse aperture 170 should have minimal dimensions to maximize the strength and structural integrity of the implant 101. On the other hand, the transverse aperture 70 should have maximum dimensions to (a) improve the visibility of the implant 101 during surgical procedures to ensure proper implant placement and seating, and to improve post-operative assessment of implant fusion, and (b) to facilitate engagement between bone graft material and adjacent bone. The substantially hollow area defined by the implant 101 may be filled with bone graft materials to facilitate the formation of a solid fusion column within the spine of a patient.

As shown in FIGS. 2 and 3, the transverse aperture 170 extends the entire transverse length of the implant body and nearly the entire height of the implant body. Thus, the size and shape of the transverse aperture 170 approach the maximum possible dimensions for the transverse aperture 170.

The transverse aperture 170 may be broken into two, separate sections by an intermediate wall 172. The section of the transverse aperture 170 proximate the IHF 194 is substantially rectangular in shape; the other section of the transverse aperture 170 has the shape of a curved arch. Other shapes and dimensions are suitable for the transverse aperture 170. In particular, all edges of the transverse aperture 170 may be rounded, smooth, or both. The intermediate wall 172 may be made of the same material as the remainder of the implant 101 (e.g., metal), or it may be made of another material (e.g., PEEK) to form a composite implant 101. The intermediate wall 172 may offer one or more of several advantages, including reinforcement of the implant 101 and improved bone graft containment.

The embodiment of the invention illustrated in FIGS. 2 and 3 is especially well suited for a PLIF surgical procedure. TLIF surgery is done through the posterior (rear) part of the spine and is essentially like an extended PLIF procedure. The TLIF procedure was developed in response to some of the technical problems encountered with a PLIF procedure. The main difference between the two spine fusion procedures is that the TLIF approach to the disc space is expanded by removing one entire facet joint; a PLIF procedure is usually done on both sides by only taking a portion of each of the paired facet joints.

By removing the entire facet joint, visualization into the disc space is improved and more disc material can be removed. Such removal should also provide for less nerve retraction. Because one entire facet is removed, the TLIF procedure is only done on one side: removing the facet joints on both sides of the spine would result in too much instability. With increased visualization and room for dissection, one or both of a larger implant and more bone graft can be used in the TLIF procedure. Theoretically, these advantages can allow the spine surgeon to distract the disc space more and realign the spine better (re-establish the normal lumbar lordosis).

Although the TLIF procedure offers some improvements over a PLIF procedure, the anterior approach in most cases still provides the best visualization, most surface area for healing, and the best reduction of any of the approaches to the disc space. These advantages must be weighed, however, against the increased morbidity (e.g., unwanted aftereffects and postoperative discomfort) of a second incision. Probably the biggest determinate in how the disc space is approached is the comfort level that the spine surgeon has with an anterior approach for the spine fusion surgery. Not all spine surgeons are comfortable with operating around the great vessels (aorta and vena cava) or have access to a skilled vascular surgeon to help them with the approach. Therefore, choosing one of the posterior approaches for the spine fusion surgery is often a more practical solution.

Figure 4:
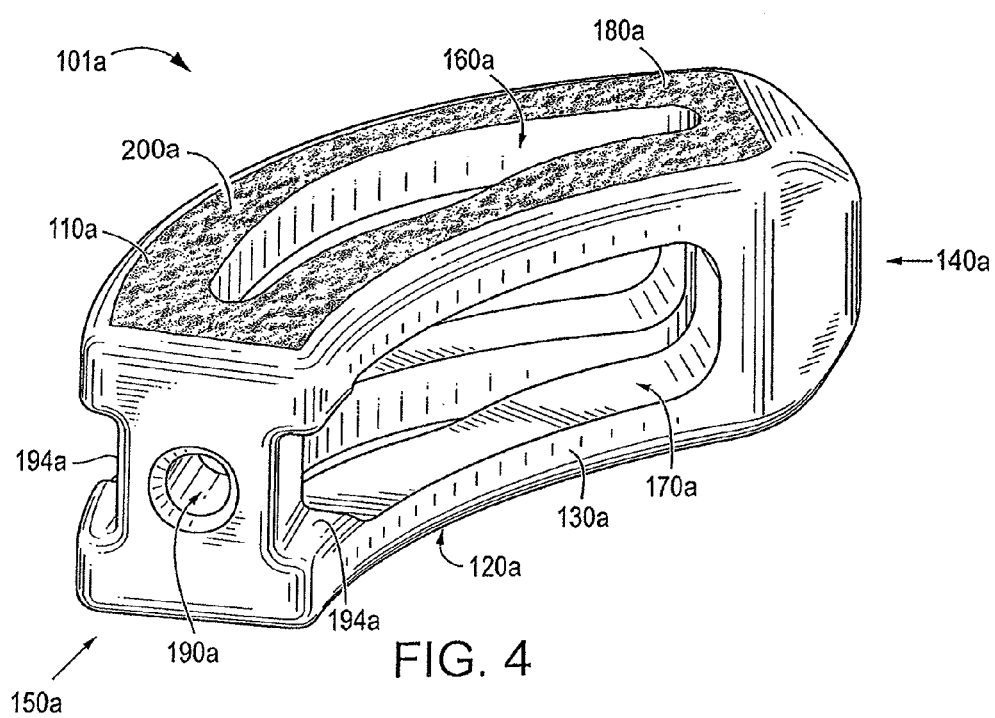
FIG. 4 shows a perspective view from the front of yet another embodiment of the interbody spinal implant according to the invention.
Figure 5:
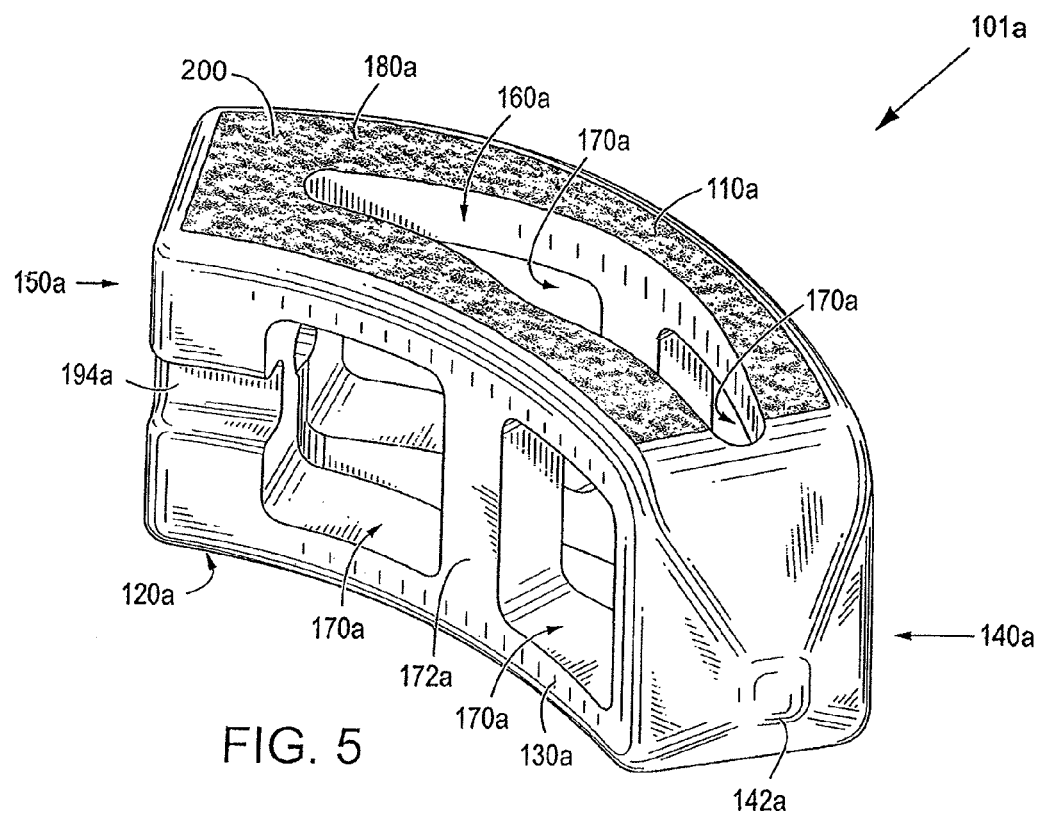
FIG. 5 shows a perspective view from the rear of the embodiment of the interbody spinal implant illustrated in FIG. 4 highlighting an alternative transverse aperture.

The embodiment of the invention illustrated in FIGS. 4 and 5 is especially well suited when the spine surgeon elects a TLIF procedure. Many of the features of the implant 101a illustrated in FIGS. 4 and 5 are the same as those of the implant 101 illustrated in FIGS. 2 and 3. Therefore, these features are given the same reference numbers, with the addition of the letter "a," and are not described further.

There are several differences, however, between the two embodiments. For example, unlike the substantially rectangular shape of the implant 101, the implant 101a has a curved shape. Further, the chamfers 106 and anti-expulsion edge 108 of the implant 101 are replaced by curves or rounded edges for the implant 101a. Still further, the TLIF procedure often permits use of a larger implant 101a which, in turn, may affect the size and shape of the predetermined vertical aperture 160a.

The substantially constant 9 mm width of the transverse rim 200 of the implant 101 is replaced with a larger, curved transverse rim 200a. The width of the transverse rim 200a is 9 mm in the regions adjacent the anterior 140a and posterior 150a portions. That width gradually increases to 11 mm, however, near the center of the transverse rim 200a. The additional real estate provided by the transverse rim 200a (relative to the transverse rim 200) allows the shape of the vertical aperture 160a to change, in cross section, from approximating a football to approximating a boomerang.

The implant 101a may also have a lordotic angle to facilitate alignment. The lateral side 130a depicted at the top of the implant 101a is preferably generally greater in height than the opposing lateral side 130a. Therefore, the implant 101a may better compensate for the generally less supportive bone found in certain regions of the vertebral endplate.

As shown in FIG. 4, the transverse aperture 170a extends the entire transverse length of the implant body and nearly the entire height of the implant body. FIG. 5 highlights an alternative transverse aperture 170a. As illustrated in FIG. 5, the transverse aperture 170a is broken into two, separate sections by an intermediate wall 172a. Thus, the dimensions of the transverse aperture 170a shown in FIG. 5 are much smaller than those for the transverse aperture 170a shown in FIG. 4. The two sections of the alternative transverse aperture 170a are each illustrated as substantially rectangular in shape and extending nearly the entire height of the implant body; other sizes and shapes are possible for one or both sections of the alternative transverse aperture 170a.

The intermediate wall 172a may be made of the same material as the remainder of the implant 101a (e.g., metal), or it may be made of another material (e.g., PEEK) to form a composite implant 101a. It is also possible to extend the intermediate wall 172a, whether made of metal, PEEK, ultra-high molecular weight polyethylene (UHMWPE), or another material, to eliminate entirely the transverse aperture 170a. Given the reinforcement function of the intermediate wall 172a, the length of the vertical aperture 160a can be extended (as shown in FIG. 5) beyond the top surface 110a and into the anterior portion 140a of the implant 101a.

The top surface 110a of the implant 101a need not include the roughened topography 180a. This difference permits the implant 101a, at least for certain applications, to be made entirely of a non-metal material. Suitable materials of construction for the implant 101a of such a design (which would not be a composite) include PEEK, hedrocel, UHMWPE, other radiolucent soft plastics, and additional materials as would be known to an artisan.

The embodiments of the invention described above are best suited for one or more of the ALIF, PLIF, and TLIF surgical procedures. Another embodiment of the invention is better suited for cervical fusion procedures. This embodiment is illustrated in FIGS. 6 and 7 as the interbody spinal implant 201.

Because there is not a lot of disc material between the vertebral bodies in the cervical spine, the discs are usually not very large. The space available for the nerves is also not that great, however, which means that even a small cervical disc herniation may impinge on the nerve and cause significant pain. There is also less mechanical load on the discs in the cervical spine as opposed to the load that exists lower in the spine. Among others, these differences have ramifications for the design of the implant 201.

The implant 201 is generally smaller in size than the other implant embodiments. In addition, the lower mechanical load requirements imposed by the cervical application typically render a composite implant unnecessary. Therefore, the implant 201 is generally made entirely of metal (e.g., titanium) and devoid of other materials (e.g., PEEK).

Figure 6:
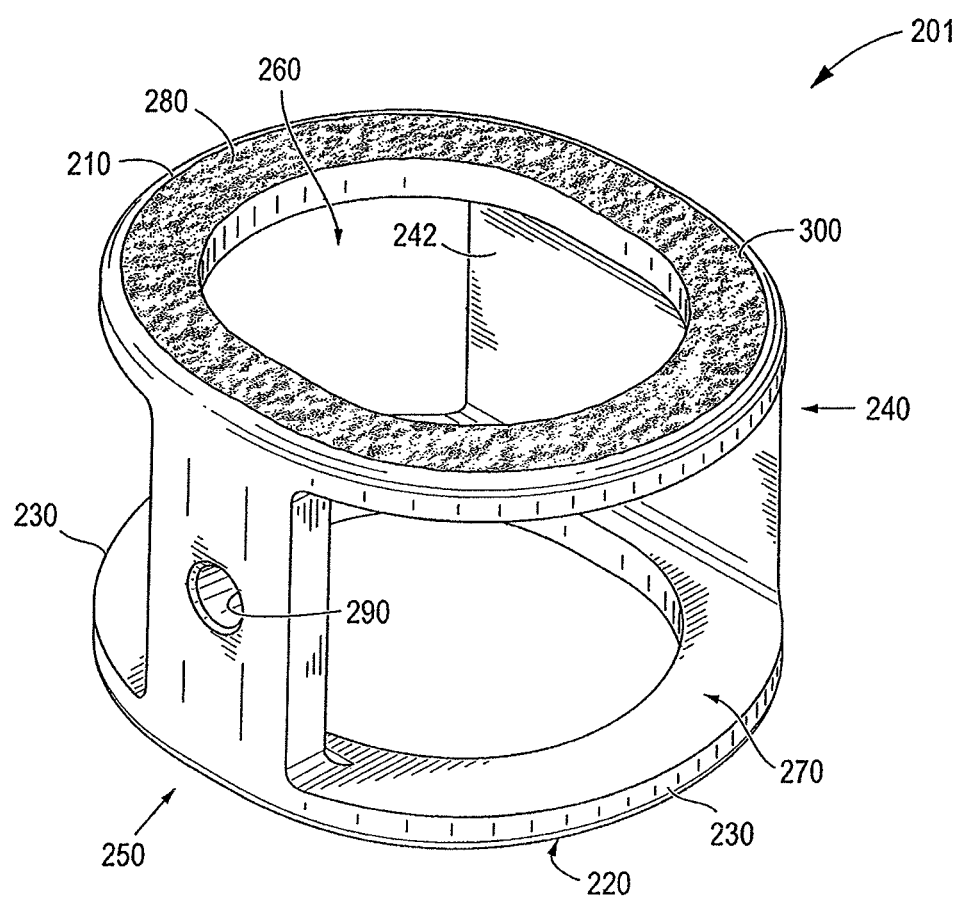
FIG. 6 shows a perspective view of another embodiment of the interbody spinal implant having a generally oval shape and being especially well adapted for use in a cervical spine surgical procedure.
Figure 7:
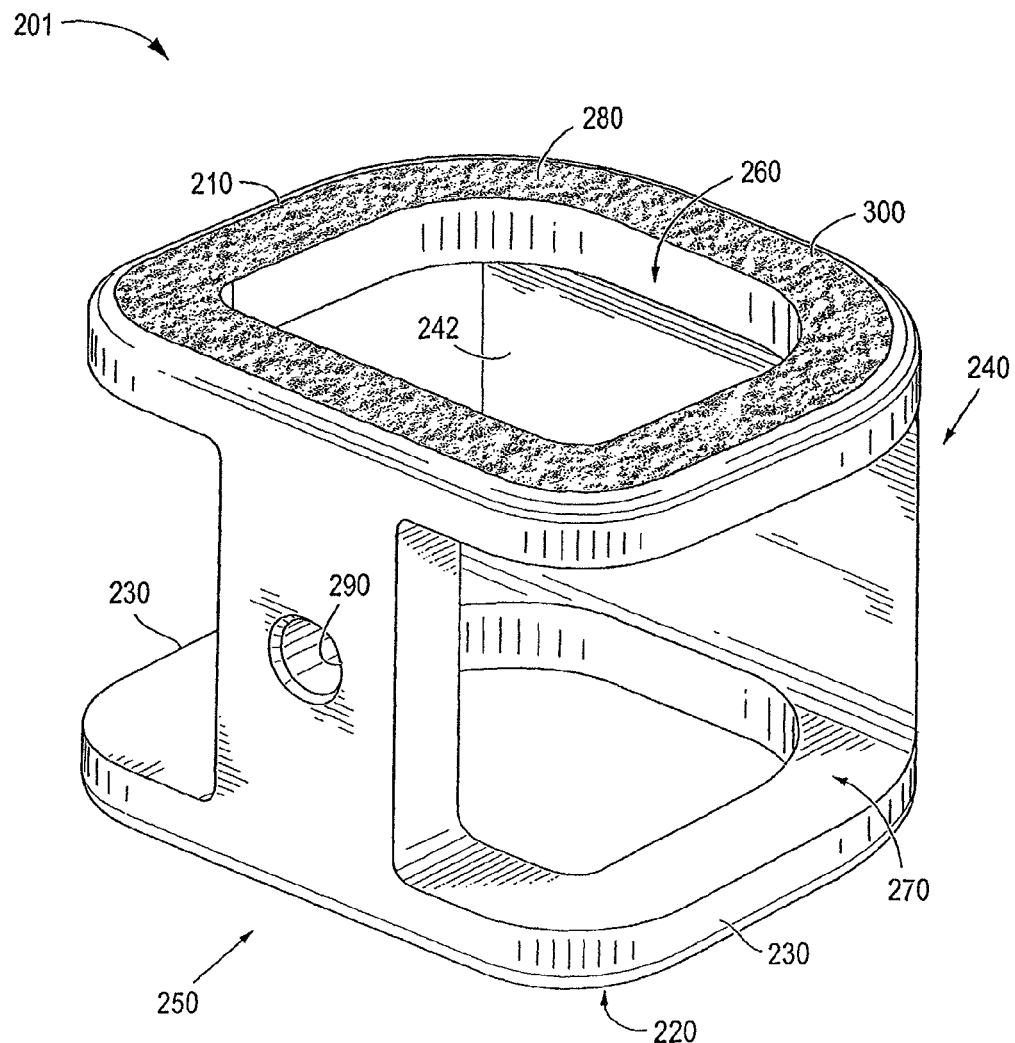
FIG. 7 shows a perspective view of an implant having a generally box shape.
Figure 8:
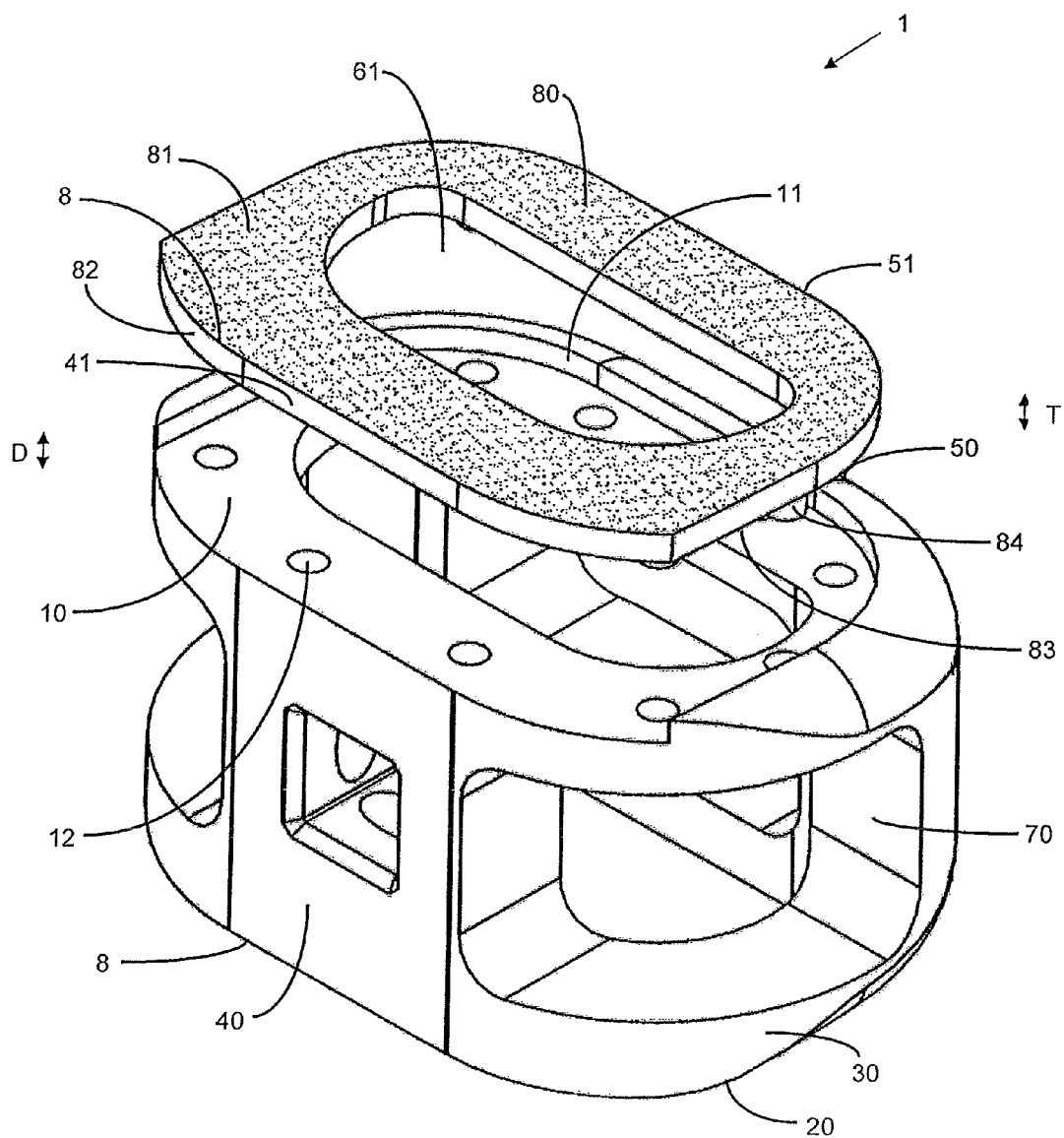
FIG. 8 shows an exploded view of a generally oval-shaped implant with an integration plate.

With specific reference to FIG. 6, the implant 201 includes a body having a top surface 210, a bottom surface 220, opposing lateral sides 230, and opposing anterior 240 and posterior 250 portions. One or both of the top surface 210 and the bottom surface 220 has a roughened topography 280 for gripping adjacent bone and inhibiting migration of the implant 201. The implant 201 is substantially hollow and has a generally oval shape with smooth, rounded, or both smooth and rounded edges.

The implant 201 includes at least one vertical aperture 260 that extends the entire height of the implant body. The vertical aperture 260 further defines a transverse rim 300.

As illustrated in FIG. 6, the implant 201 has an opening 290 in the posterior portion 250. The opening 290 has a number of functions. One function is to facilitate manipulation of the implant 201 by the caretaker. Thus, the caretaker may insert a surgical tool into the opening 290 and, through the engagement between the surgical tool and the opening 290, manipulate the implant 201. The opening 290 may be threaded to enhance the engagement.

The implant 201 may further include at least one transverse aperture 270. Like the vertical aperture 260, the size and shape of the transverse aperture 270 are carefully chosen (and predetermined) to achieve a preferable design tradeoff for the particular application envisioned for the implant 201. For example, as shown in FIG. 6, the transverse aperture 270 may extend the entire transverse length of the implant body and nearly the entire height of the implant body. Thus, the size and shape of the transverse aperture 270 approach the maximum possible dimensions for the transverse aperture 270.

As illustrated in FIG. 6, the implant 201 may be provided with a solid rear wall 242. The rear wall 242 extends the entire width of the implant body and nearly the entire height of the implant body. Thus, the rear wall 242 essentially closes the anterior portion 240 of the implant 201. The rear wall 242 may offer one or more of several advantages, including reinforcement of the implant 201 and improved bone graft containment. In the cervical application, it may be important to prevent bone graft material from entering the spinal canal.

Alternative shapes for the implant 201 are possible. As illustrated in FIG. 7, for example, the implant 201 may have a generally box shape which gives the implant 201 increased cortical bone coverage. Like the implant 201 shown in FIG. 6, the implant 201 shown in FIG. 7 has a curved transverse rim 300 in the area of the anterior portion 240. The shape of the posterior portion 250 of the implant 201 is substantially flat, however, and the shape of the transverse rim 300 in the area of the posterior portion 250 is substantially square. Thus, the posterior portion 250 provides a face that can receive impact from a tool, such as a surgical hammer, to force the implant 201 into position.

The implant 201 may also have a lordotic angle to facilitate alignment. As illustrated in FIGS. 6 and 7, the anterior portion 240 is preferably generally greater in height than the posterior portion 250. Therefore, the implant 201 may better compensate for the generally less supportive bone found in certain regions of the vertebral endplate. As an example, four degrees of lordosis may be built into the implant 201 to help restore balance to the spine.

Certain embodiments of the implant 1, 101, 101a, and 201 are generally shaped (i.e., made wide) to maximize contact with the apophyseal rim of the vertebral endplates. They are designed to be impacted between the endplates, with fixation to the endplates created by an interference fit and annular tension. Thus, the implants 1, 101, 101a, and 201 are shaped and sized to spare the vertebral endplates and leave intact the hoop stress of the endplates. A wide range of sizes are possible to capture the apophyseal rim, along with a broad width of the peripheral rim, especially in the posterior region. It is expected that such designs will lead to reduced subsidence. As much as seven degrees of lordosis (or more) may be built into the implants 1, 101, 101a, and 201 to help restore cervical balance.

When endplate-sparing spinal implant 1, 101, 101a, and 201 seats in the disc space against the apophyseal rim, it should still allow for deflection of the endplates like a diaphragm. This means that, regardless of the stiffness of the spinal implant 1, 101, 101a, and 201, the bone graft material inside the spinal implant 1, 101, 101a, and 201. receives load, leading to healthy fusion. The vertical load in the human spine is transferred though the peripheral cortex of the vertebral bodies. By implanting an apophyseal-supporting inter-body implant 1, 101, 101a, and 201, the natural biomechanics may be better preserved than for conventional devices. If this is true, the adjacent vertebral bodies should be better preserved by the implant 1, 101, 101a, and 201, hence reducing the risk of adjacent segment issues.

In addition, the dual-acid etched roughened topography 80, 180, 180a, and 280 of the top surface 30, 130, 130a, and 230 and the bottom surface 40, 140, 140a, and 240 along with the broad surface area of contact with the end-plates, is expected to yield a high pull-out force in comparison to conventional designs. As enhanced by the sharp edges 8 and 108, a pull-out strength of up to 3,000 nt may be expected. The roughened topography 80, 180, 180a, and 280 creates a biological bond with the end-plates over time, which should enhance the quality of fusion to the bone. Also, the in-growth starts to happen much earlier than the bony fusion. The center of the implant 1, 101, 101a, and 201 remains open to receive bone graft material and enhance fusion. Therefore, it is possible that patients might be able to achieve a full activity level sooner than for conventional designs.

The spinal implant 1, 101, 101a, and 201 according to the invention offers several advantages relative to conventional devices. Such conventional devices include, among others, ring-shaped cages made of allograft bone material, threaded titanium cages, and ring-shaped cages made of PEEK or carbon fiber.

Figure 9:
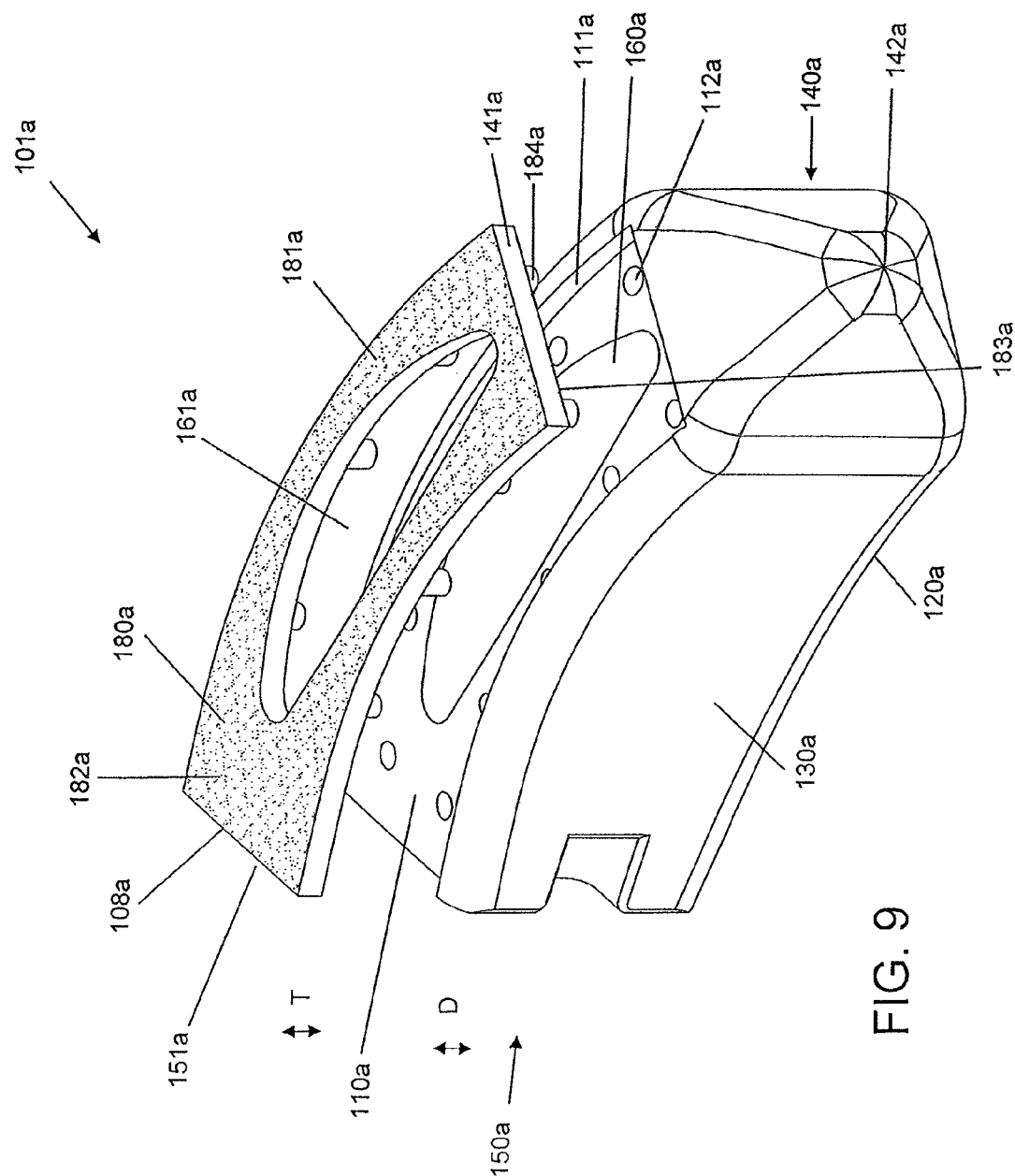
FIG. 9 shows an exploded view of a curved implant with an integration plate.
Figure 10:
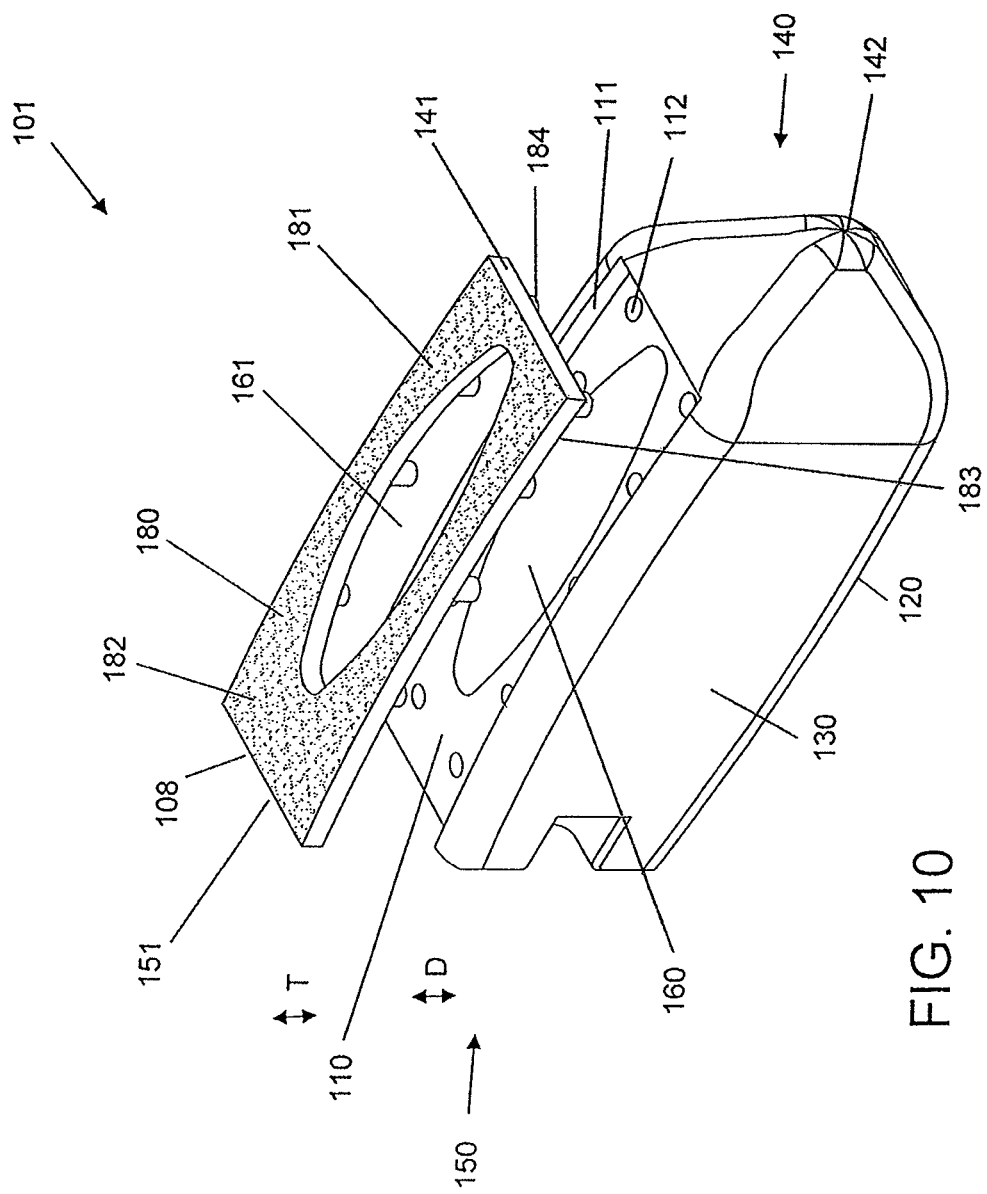
FIG. 10 shows an exploded view of a posterior implant with an integration plate.
Figure 11:
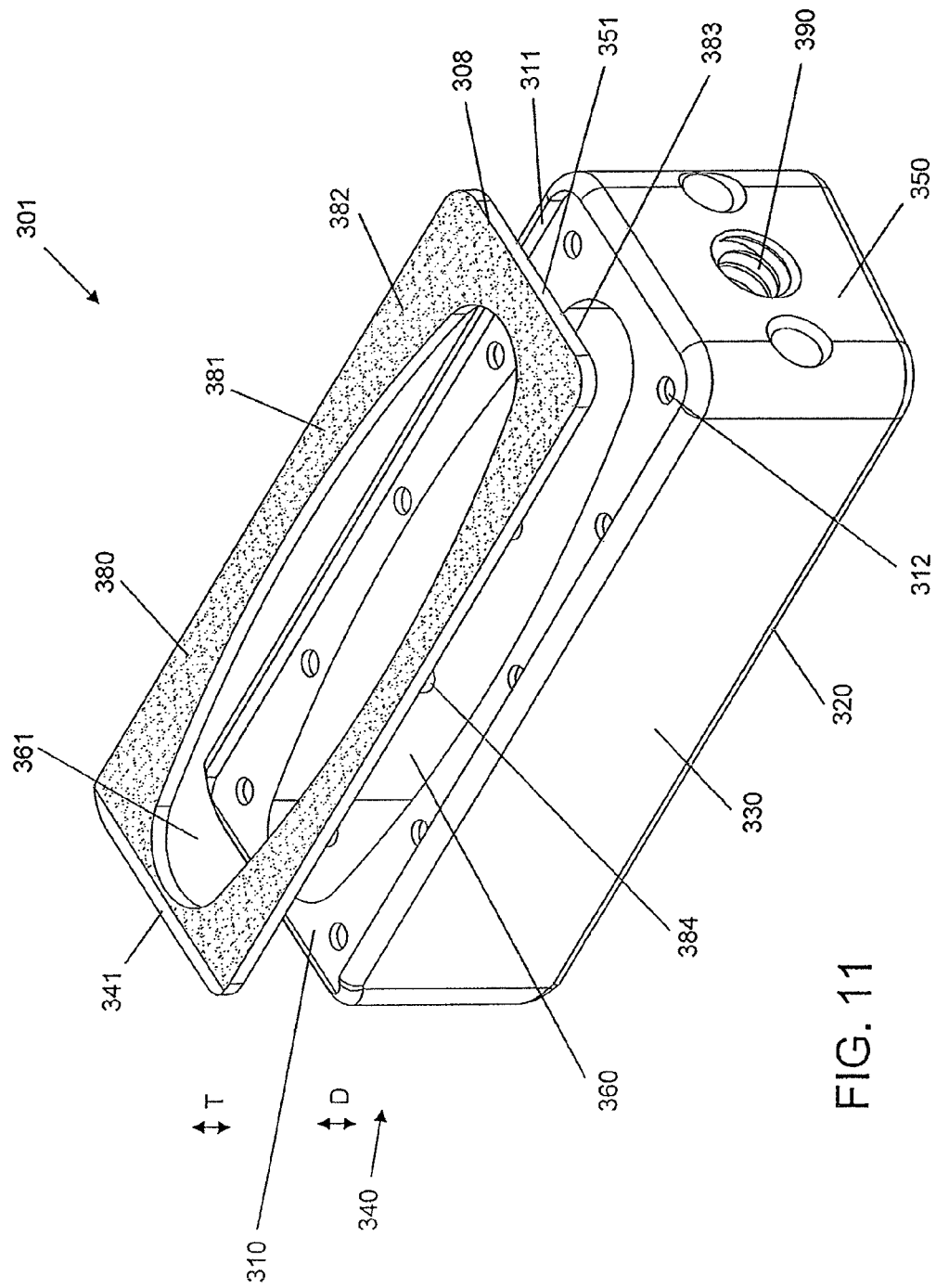
FIG. 11 shows an exploded view of a lateral lumbar implant with an integration plate.

In some aspects, the implant 1, 101, 101a, and 201 includes an integration plate 82, 182, 182a, and 282, for example, as shown in FIG. 8A-FIG. 10 and FIG. 12. In addition, a lateral implant 301 having a substantially rectangular shape may include an integration plate 382, for example, as shown in FIG. 11. The lateral implant 301 comprises the same general features as the implant 1, 101, 101a, and 201, including a top surface 310, a bottom surface 320, lateral sides 330, opposing anterior 340 and posterior 350 portions, an opening 390, as well as at least one vertical aperture 360 that extends the entire height of the implant body, and one or more transverse apertures 370 that extend the entire transverse length of the implant body.

The integration plate, shown in the drawings as component 82 (FIG. 8A and FIG. 8B), 182 (FIG. 10), 182a (FIG. 9), 382 (FIGS. 11), and 282 (FIG. 12), respectively, includes the roughened surface topography 80, 180, 180a, 280, and 380, and is connectable to either or both of the top surface 10, 110, 110a, 210, and 310 or bottom surface 20, 120, 120a, 220, and 320. The integration plate 82, 182, 182a, 282, and 382 includes a top surface 81, 181, 181a, 281, and 381; a bottom surface 83, 183, 183a, 283, and 383; an anterior portion 41, 141, 141a, 241, and 341; a posterior portion 51, 151, 151a, 251, and 351; and at least one vertical aperture 61, 161, 161a, 261, and 361. The anterior portion 41, 141, 141a, 241, and 341 preferably aligns with the anterior portion 40, 140, 140a, 240, and 340 of the main body of the implant 1, 101, 101a, 201, and 301, respectively, and the posterior portion 51, 151, 151a, 251, and 351 aligns with the posterior portion 50, 150, 150a, 250, and 350 of the main body of the implant 1, 101, 101a, 201, and 301, respectively. The vertical aperture 61, 161, 161a, 261, and 361 preferably aligns with the vertical aperture 60, 160, 160a, 260, and 360 of the main body of the implant 1, 101, 101a, 201, and 301, respectively. Thus, the integration plate vertical aperture 61, 161, 161a, 261, and 361 and the body vertical aperture 60, 160, 160a, 260, and 360 preferably comprise substantially the same shape.

The top surface 81, 181, 181a, 281, and 381 of the integration plate 82, 182, 182a, 282, and 382 preferably comprises the roughened topography 80, 180, 180a, 280, and 380. The bottom surface 83, 183, 183a, 283, and 383 of the integration plate 82, 182, 182a, 282, and 382 preferably comprises a reciprocal connector structure, such as a plurality of posts 84, 184, 184a, 284, and 384 that align with and insert into a corresponding connector structure such as a plurality of holes 12, 112, 112a, 212, and 312 on the top surface 10, 110, 110a, 210, and 310 and/or bottom surface 20, 120, 120a, 220, and 320 of the main body of the implant 1, 101, 101a, 201, and 301, respectively, and thus facilitate the connection between the integration plate 82, 182, 182a, 282, and 382 and the main body of the implant 1, 101, 101a, 201, and 301. Thus, integration plates 82, 182, 182a, 282, and 382 with different sizes, shapes, or features may be used in connection with the implant 1, 101, 101a, 201, and 301, for example, to accommodate attributes of the spine of the patient to which the implant 1, 101, 101a, 201, and 301 is to be implanted. Among these different sizes, shapes, and features are lordotic angles;

anti-expulsion edges 8, 108, 108a, 208, and 308; and anti-expulsion angles as described throughout this specification.

The implant 1, 101, 101a, 201, and 301 is configured to receive the integration plate 82, 182, 182a, 282, and 382, respectively. Thus, for example, the top surface 10, 110, 110a, 210, and 310 and/or bottom surface 20, 120, 120a, 220, and 320 of the implant 1, 101, 101a, 201, and 301 may be recessed, and comprise a plurality of holes 12, 112, 112a, 212, and 312 that mate with the plurality of posts 84, 184, 184a, 284, and 384 on the bottom surface 83, 183, 183a, 283, and 383 of the integration plate 82, 182, 182a, 282, and 382. Thus, the plurality of posts 84, 184, 184a, 284, and 384 are inserted into the plurality of holes 12, 112, 112a, 212, and 312.

Figure 12:
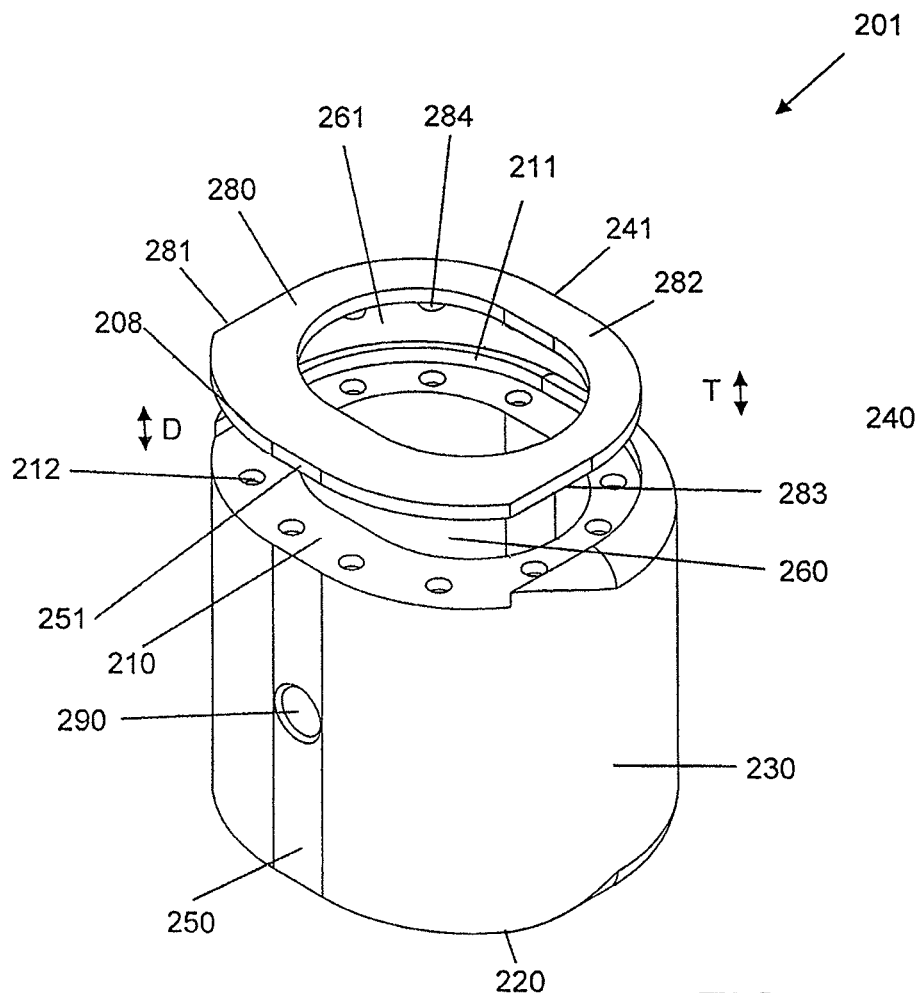
FIG. 12 shows an exploded view of a generally oval-shaped anterior cervical implant with an integration plate.

FIG. 8A and FIG. 8B show that the top surface 10 is recessed and comprises a plurality of holes 12, but the recessed bottom surface 20 and its holes 12 are not shown. FIG. 9 shows that the top surface 110a is recessed and comprises a plurality of holes 112a, but the recessed bottom surface 120a and its holes 112a are not shown. FIG. 10 shows that the top surface 110 is recessed and comprises a plurality of holes 112, but the recessed bottom surface 120 and its holes 112 are not shown. FIG. 11 shows that the top surface 310 is recessed and comprises a plurality of holes 312, but the recessed bottom surface 320 and its holes 312 are not shown. FIG. 12 shows that the top surface 210 is recessed and comprises a plurality of holes 212, but the recessed bottom surface 220 and its holes 212 are not shown. The recess may be at a depth D, and the recess depth D preferably is uniform throughout the top surface 10, 110, 110a, 210, and 310 and/or bottom surface 20, 120, 120a, 220, and 320.

The recess depth D preferably corresponds to a thickness T of the integration plate 82, 182, 182a, 282, and 382. Thus, in some aspects, the depth D and thickness T are the same so that once the integration plate 82, 182, 182a, 282, and 382 and body of the implant 1, 101, 101a, 201, and 301, respectively, are placed together, the top surface 10, 110, 110a, 210, and 310 and/or bottom surface 20, 210, 120a, 220, and 320 of the implant 1, 101, 101a, 201, and 301 is substantially even, at least at the seam/junction between the integration plate 82, 182, 182a, 282, and 382 and the top surface 10, 110, 110a, 210, and 310 or bottom surface 20, 210, 120a, 220, and 320. In some embodiments, the posterior portion 51, 151, 151a, 251, and 351 and the anterior portion 41, 141, 141a, 241, and 341 of the integration plate 82, 182, 182a, 282, and 382 have different thicknesses such that the anterior portion 41, 141, 141a, 241, and 341 has a greater thickness than the thickness T of the posterior portion 51, 151, 151a, 251, and 351.

The recess depth D, the thickness T, and the thickness T' may each independently be from about 0.1 mm to about 10 mm. In preferred aspects, the recess depth D, the thickness T, and the thickness T' may each independently be from about 1 mm to about 5 mm. Thus, for example, either the recess depth D, the thickness T, and the thickness T' may be selected from about 0.1 mm, about 0.25 mm, about 0.5 mm, about 0.75 mm, about 1 mm, about 1.25 mm, about 1.5 mm, about 1.75 mm, about 2 mm, about 2.25 mm, about 2.5 mm, about 2.75 mm, about 3 mm, about 3.25 mm, about 3.5 mm, about 3.75 mm, about 4 mm, about 4.25 mm, about 4.5 mm, about 4.75 mm, about 5 mm, 5.5 mm, about 6 mm, about 6.5 mm, about 7 mm, about 75 mm, or about 8 mm.

Recessing the top surface 10, 110, 110a, 210, and 310 or bottom surface 20, 120, 120a, 220, and 320 exposes a ridge 11, 111, 111a, 211, and 311 against which the anterior portion 41, 141, 141a, 241, and 341, posterior portion 51, 151, 151a, 251, and 251 or lateral side of the integration plate 82, 182, 182a, 282, and 382 may be seated when brought together with the implant 1, 101, 101a, 201, and 301.

The integration plate 82, 182, 182a, 282, and 382 may be used with an implant suitable for ALIF (e.g., implant 1, integration plate 82), PLIF (e.g., implant 101, integration plate 182), or TLIF fusion (e.g., implant 101a, integration plate 182a); may be used with an implant suitable for cervical fusion (e.g., implant 201, integration plate 282); and may be used with an implant suitable for lateral lumbar insertion (e.g., implant 301, integration plate 382). The integration plate 82, 182, 182a, 282, and 382 is preferably metal, and may be used with a metal implant. The metal integration plate 82, 182, 182a, 282, and 382 may also be used with a molded plastic or polymer implant, or a composite implant. In some aspects, the integration plate 82, 182, 182a, 282, and 382 may also comprise a plastic, polymeric, or composite material.

The reciprocal connector such as the post 84, 184, 184a, 284, and 384 preferably is secured within the connector of the body such as the hole 12, 112, 112a, 212, and 312 to mediate the connection between the integration plate 82, 182, 182a, 282, and 382 and the implant 1, 101, 101a, 201, and 301. The connection should be capable of withstanding significant loads and shear forces when implanted in the spine of the patient. The connection between the post 84, 184, 184a, 284, and 384 and the hole 12, 112, 112a, 212, and 312 may comprise a friction fit. In some aspects, an adhesive may be used to further strengthen any of the integration plate 82, 182, 182a, 282, and 382 and implant 1, 101, 101a, 201, and 301 connections. An adhesive may comprise a cement, glue, polymer, epoxy, solder, weld, or other suitable binding material.

Figure 13A:
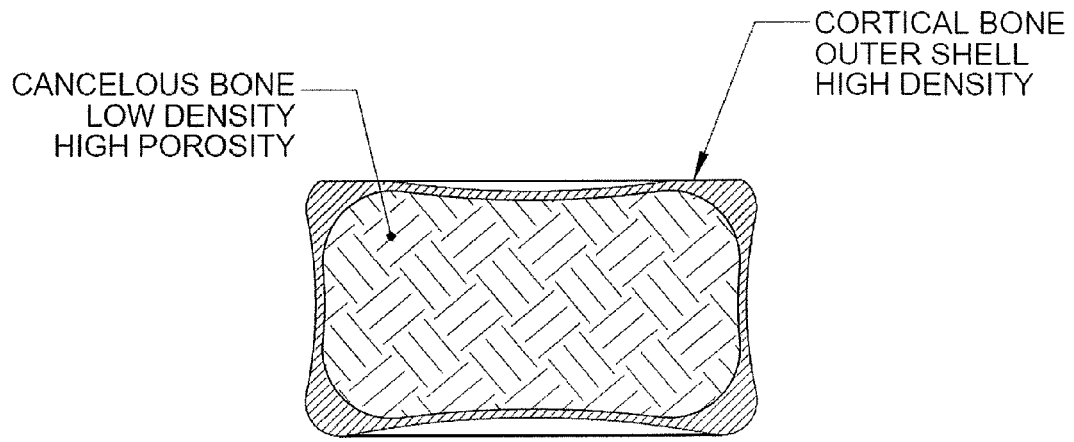
FIG. 13A shows a representation of a cross section of a vertebrae.
Figure 13B:
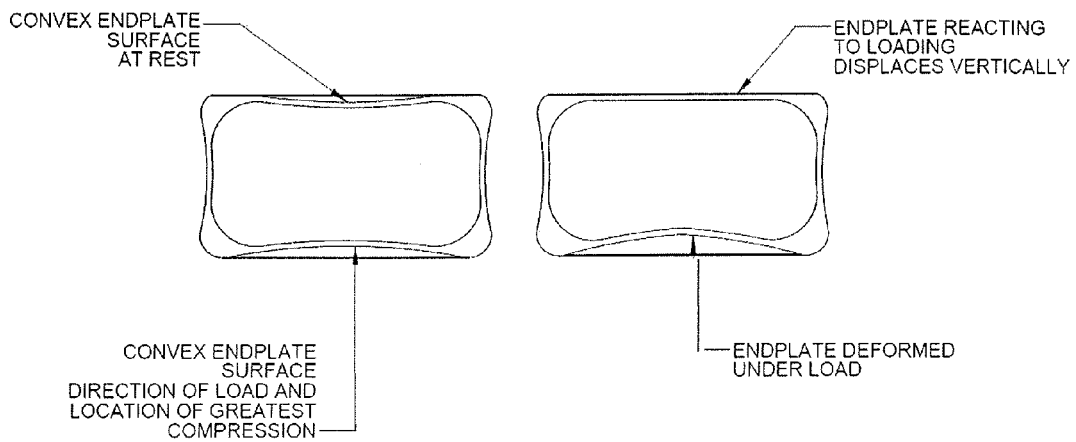
FIG. 13B shows a representation of load-based deformation of vertebral endplate surfaces.

Vertebrae comprise a high density, cortical bone exterior that surrounds a low density and highly porous cancellous bone core, for example, as illustrated graphically in FIG. 13A. Cortical bone is part of the vertebral endplate surface, and a disc occupies the space between opposing vertebral endplate surfaces (e.g., the intervertebral space). Movement, including walking, lifting, and other activities that implicate movement and flexing of the spine produce load forces that impact disc material, but also induce flexing and compression of the vertebral endplate surfaces. For example, under load stress, the cortical bone of the vertebral endplate surface may flex inward toward the core of the vertebrae or outward toward the disc in the intervertebral space. Flexing of the endplate is shown graphically in FIG. 13B, though it is to be understood that FIG. 13B is provided for illustration purposes only, and is not intended to be limiting in any way. The left panel of FIG. 13B shows an unloaded vertebrae, with each endplate slightly concave. The right panel of FIG. 13B shows the endplate reacting to load forces, with a reduced concave shape of the top portion, and an enhanced concave shape of the bottom portion. The capacity of vertebral endplate bone to flex under load forces may be exploited to facilitate implantation and integration of the implant 1, 101, 101a, 201, and 301.

Each implant 1, 101, 101a, 201, and 301 includes a vertical aperture 60, 160, 160a, 260, and 360 extending through the implant 1, 101, 101a, 201, and 301. Into this vertical aperture 60, 160, 160a, 260, and 360, a bone graft material is preferably placed and housed during implantation. The bone graft material may be cancellous autograft bone, allograft bone, demineralized bone matrix (DBM), porous synthetic bone graft substitute, bone morphogenic protein (BMP), or a combination thereof, and this bone graft material is used to facilitate fusion with the spine. Preferably, the bone graft material initiates, enhances, and/or otherwise supports new bone growth, and osteointegration of the spine and the implant 1, 101, 101a, 201, and 301. Thus, it is highly preferred that the bone graft material establishes and maintains contact with the vertebral endplate bone of the vertebrae between which the implant 1, 101, 101*a*, 201, and 301 has been placed.

To establish and maintain contact between the bone graft material and the vertebral endplate bone, the location, direction, and extent, among other aspects, of flexing of vertebral endplate bone under load stress, and under normal conditions may be taken into account. For example, the practitioner may position the implant 1, 101, 101*a*, 201, and 301 in the intervertebral space at a loci where the bone graft material exposed through the vertical aperture 60, 160, 160*a*, 260, and 360 may make maximal contact with vertebral endplate bone, whether at rest/under normal conditions, or under particular load stress. As well, the practitioner may use excess graft material such that the graft material extends beyond the top surface 10, 110, 110*a*, 210, and 310 and/or bottom surface 20, 120, 120*a*, 220, and 320 of the implant 1, 101, 101*a*, 201, and 301. The surface of the excess graft material may thus establish, and preferably maintain, contact the vertebral endplate bone.

Flexing of the vertebral endplate bone may facilitate contact with the excess graft material, for example, by compressing the graft material and spreading the graft material outward, thereby expanding the surface area of the graft material and allowing the graft material to contact more vertebral endplate bone. In some aspects, both placement/loci of the implant 1, 101, 101*a*, 201, and 301 and the use of excess graft material may combine to establish and maintain contact between the bone graft material and the vertebral endplate bone.

Figure 14A:
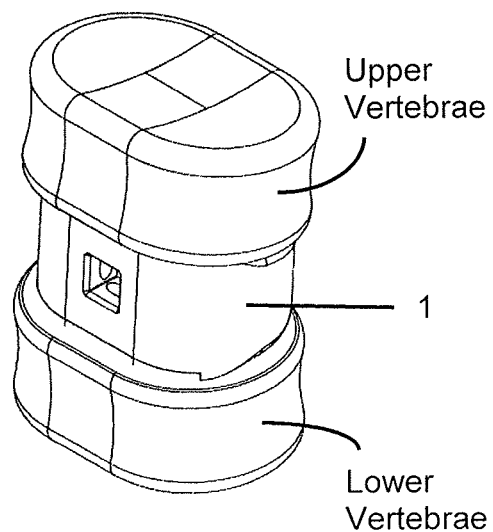
FIG. 14A shows a perspective view of an implant secured in place between adjacent vertebrae.
Figure 14B:
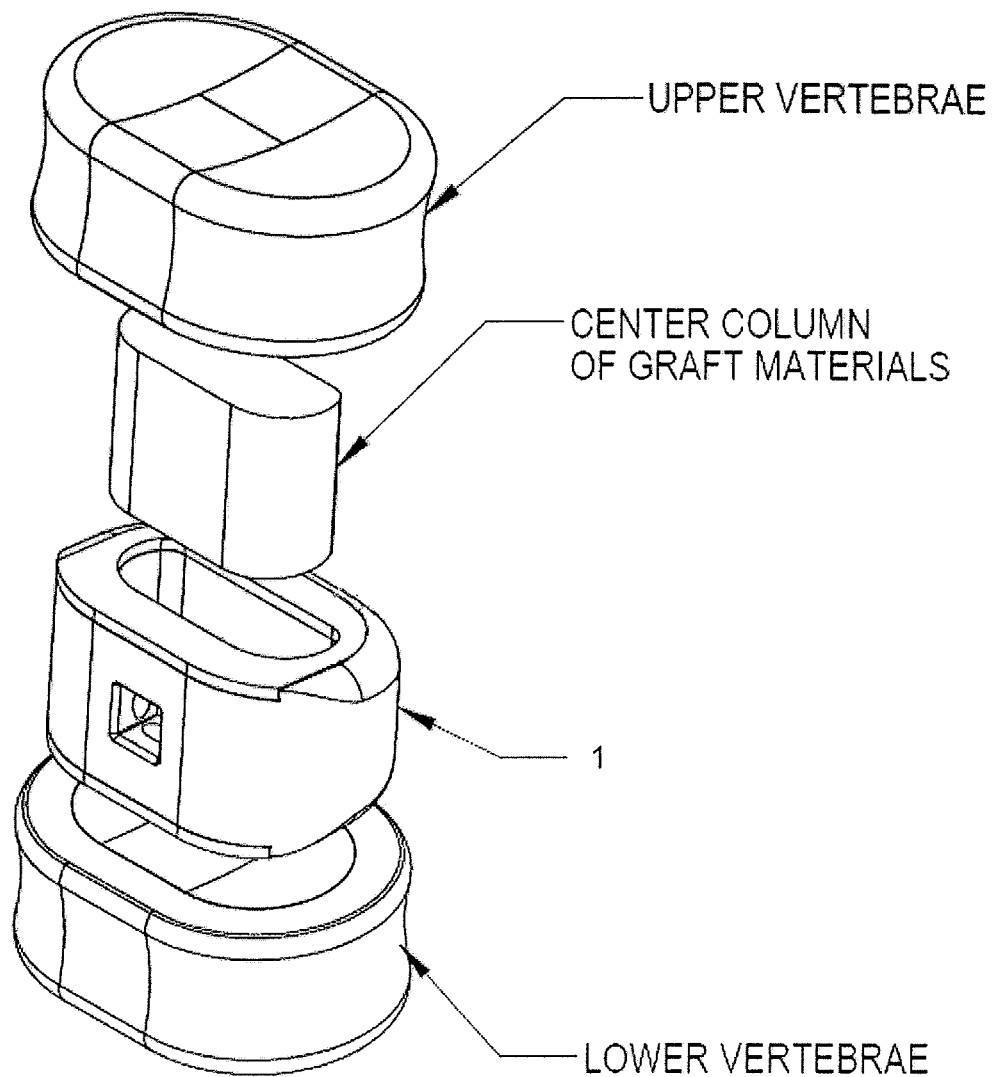
FIG. 14B shows an exploded view of the perspective view shown in FIG. 14A, with the implant having bone graft material placed between adjacent vertebrae.
Figure 14C:
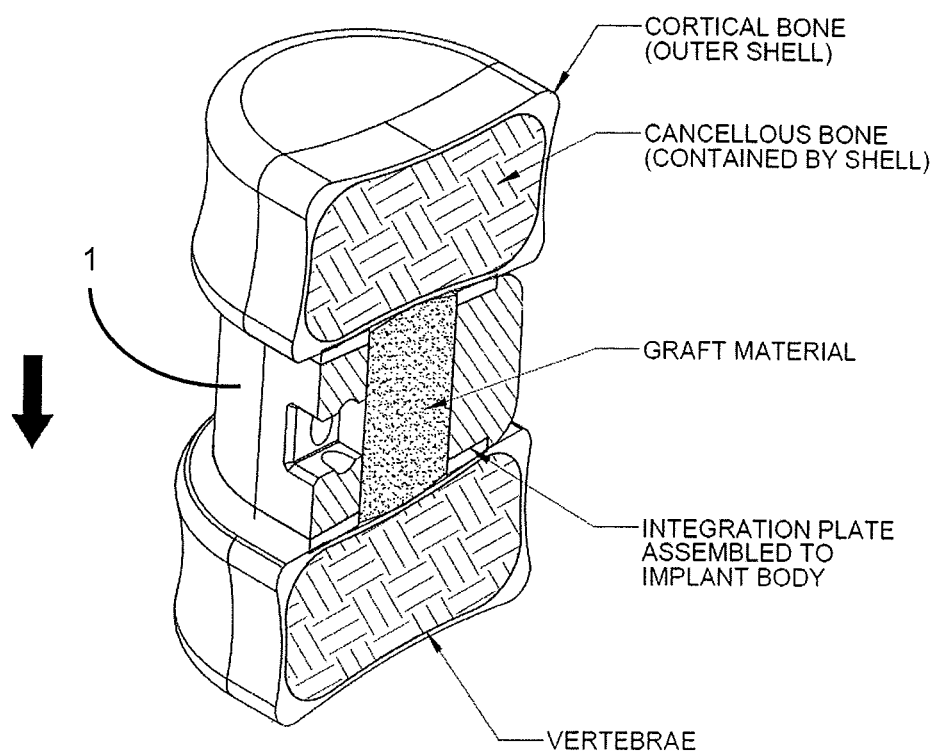
FIG. 14C shows a cut-away view of the perspective view shown in FIG. 14A.

FIG. 14A shows a representation of the implant 1 seated in place between two vertebrae, with the implant 1 containing bone graft material (not shown). The implant 1, which does not occupy the full intervertebral space, is inserted to facilitate contact between the graft material and the vertebral endplate bone, as illustrated in the exploded view of FIG. 14B. The cut-away view shown in FIG. 14C demonstrates that excess graft material "overflows" from the top surface 10 and bottom surface 20 of the implant 1, and makes contact with the vertebral endplate surface. The arrow in FIG. 14C shows the direction of load stress from walking or lifting movement.

The configuration of the implant 1, 101, 101*a*, 201, and 301 itself may facilitate contact between the bone graft material and the vertebral endplate surfaces. For example, the vertical aperture 60, 160, 160*a*, 260, and 360 may be lengthened and/or widened and/or positioned in different locations about the top surface 10, 110, 110*a*, 210, and 310 and/or bottom surface 20, 120, 120*a*, 220, and 320. For example, with respect to varying the position, the vertical aperture 60, 160, 160*a*, 260, and 360 may be positioned substantially in the center of the body of the implant 1, 101, 101*a*, 201, and 301, or may be positioned off-center, such as toward the anterior 40, 140, 140*a*, 240, and 340, or the posterior 50, 150, 150*a*, 250, and 350, or one of the lateral sides 30, 130, 130*a*, 230, and 330. In some aspects, the shape of the vertical aperture 60, 160, 160*a*, 260, and 360 may be varied, for example, the shape may comprise a substantially circular, elliptical, diamond, triangular, rectangular, quadrilateral, or polygonal shape, or may comprise an irregular shape.

In some aspects, the implant 1, 101, 101*a*, 201, and 301 comprises an integration plate 82, 182, 182*a*, 282, and 382 on either or both of the top surface 10, 110, 110*a*, 210, and 310 and bottom surface 20, 120, 120*a*, 220, and 320, and the bone graft material passes through the vertical aperture 61, 161, 161*a*, 261, and 361 of the integration plate 82, 182, 182*a*, 282, and 382. Thus, the bone graft material is loaded into the vertical aperture 61, 161, 161*a*, 261, and 361 of the integration plate 82, 182, 182*a*, 282, and 382 and the vertical aperture 60, 160, 160*a*, 260, and 360 of the implant 1, 101, 101*a*, 201, and 301. Accordingly, the practitioner may use excess graft material such that the graft material extends beyond the top surface 81, 181, 181*a*, 281, and 381 of the integration plate 82, 182, 182*a*, 282, and 382. The surface of the excess graft material may thus establish, and preferably maintain, contact the vertebral endplate bone.

As with the vertical aperture 60, 160, 160*a*, 260, and 360, the integration plate vertical aperture 61, 161, 161*a*, 261, and 361 may be lengthened and/or widened and/or positioned in different locations about the top surface 81, 181, 181*a*, 281, and 381 and/or bottom surface 83, 183, 183*a*, 283, and 383. For example, with respect to varying the position, the vertical aperture 61, 161, 161*a*, 261, and 361 may be positioned substantially in the center of the integration plate 82, 182, 182*a*, 282, and 382, or may be positioned off-center, such as toward the anterior 41, 141, 141*a*, 241, and 341, or the posterior 51, 151, 151*a*, 251, and 351, or one of the lateral sides of the integration plate 82, 182, 182*a*, 282, and 382. In some aspects, the shape of the vertical aperture 61, 161, 161*a*, 261, and 361 may be varied, for example, the shape may comprise a substantially circular, elliptical, diamond, triangular, rectangular, quadrilateral, or polygonal shape, or may comprise an irregular shape.

The vertical aperture 60, 160, 160*a*, 260, and 360 of the implant 1, 101, 101*a*, 201, and 301 preferably aligns with the integration plate vertical aperture 61, 161, 161*a*, 261, and 361. Thus each implant body vertical aperture 60, 160, 160*a*, 260, and 360 and integration plate vertical aperture 61, 161, 161*a*, 261, and 361 preferably has substantially the same length, substantially the same width, substantially the same shape, and substantially the same location on their respective surfaces.

Nevertheless, in some aspects, the integration plate vertical aperture 61, 161, 161*a*, 261, and 361 may be longer and/or wider and/or positioned differently than its implant vertical aperture 60, 160, 160*a*, 260, and 360 counterpart. For example, the vertical aperture 60, 160, 160*a*, 260, and 360 may be narrower in terms of length and width relative to the integration plate vertical aperture 61, 161, 161*a*, 261, and 361 (which are comparatively larger) such that the graft material occupies a wider surface area at its top or bottom relative to the center mass. Such a configuration may be desirable for purposes of using less bone graft material by lessening the inner volume of the implant 1, 101, 101*a*, 201, and 301 to be filled with bone graft material. In this sense, the surface area of the bone graft material that will ultimately contact vertebral endplate bone is maximized (because the integration plate vertical aperture 61, 161, 161*a*, 261, and 361 has a larger berth), while the amount of bone graft material that does not contact vertebral endplate bone, but rather occupies space in the voids of the implant 1, 101, 101*a*, 201, and 301, is minimized (because the implant vertical aperture 60, 160, 160*a*, 260, and 360 has a smaller berth). For example, the inner volume of the implant 1, 101, 101*a*, 201, and 301 may comprise a "V" shape, or an "X" or hourglass shape.

The implant vertical aperture 60, 160, 160*a*, 260, and 360 comprises dimensions and a shape, and defines a transverse rim 100 (implant 1), 200 (implant 101), 200*a* (implant 101*a*), 300 (implant 201), and 400 (implant 301). The integration plate vertical aperture 61, 161, 161*a*, 261, and 361 comprises dimensions and a shape, and defines an integration plate transverse rim 86 (implant 1), 186 (implant 101), 186*a* (implant 101*a*), 286 (implant 201), and 386 (implant 301). Each transverse rim 100, 200, 200*a*, 300, and 400 and integration plate transverse rim 86, 186, 186*a*, 286, and 386 comprise a posterior portion width P, an anterior portion width A, and a first lateral side width L, and a second lateral side width L'.

For example, the posterior portion width P may comprise the distance between the posterior edge of the implant 1, 101, 101a, 201, and 301 or posterior edge of the integration plate 82, 182, 182a, 282, and 382 and the posterior edge of the implant vertical aperture 61, 161, 161a, 261, and 361 or the integration plate vertical aperture 60, 160, 160a, 260, and 360. The transverse rim 100, 200, 200a, 300, and 400 or the transverse rim of the integration plate 86, 186, 186a, 286, and 386 effectively surrounds the vertical aperture 60, 160, 160a, 260, and 360 or 61, 161, 161a, 261, and 361, respectively.

The transverse rim 100, 200, 200a, 300, and 400 may be present on the top surface 10, 110, 110a, 210, and 310 and the bottom surface 20, 120, 120a, 220, and 320 of the implant 1, 101, 101a, 201, and 301. The transverse rim of the integration plate 86, 186, 186a, 286, and 386 may be present on the top surface 81, 181, 181a, 281, and 381 of the integration plate 82, 182, 182a, 282, and 382. The top surface 81, 181, 181a, 281, and 381 is the surface that is exposed and visible, and may make contact with vertebral endplate bone. Thus, for example, the top surface 81, 181, 181a, 281, and 381 of an integration plate 82, 182, 182a, 282, and 382 that occupies the bottom portion 20, 120, 120a, 220, and 320 is the bottom-most surface of the implant 1, 101, 101a, 201, and 301. For clarification, the top surface of the bottom integration plate is effectively the bottom surface of the implant.

The posterior portion width P may be about 1 mm to about 15 mm, including about 1 mm, about 2 mm, about 3 mm, about 4 mm, about 5 mm, about 6 mm, about 7 mm, about 8 mm, about 9 mm, about 10 mm, about 11 mm, about 12 mm, about 13 mm, about 14 mm, or about 15 mm. The anterior portion width A may be about 1 mm to about 15 mm, including about 1 mm, about 2 mm, about 3 mm, about 4 mm, about 5 mm, about 6 mm, about 7 mm, about 8 mm, about 9 mm, about 10 mm, about 11 mm, about 12 mm, about 13 mm, about 14 mm, or about 15 mm. The first lateral side width L and second lateral side width L' may each independently by about 1 mm to about 10 mm, including about 1 mm, about 2 mm, about 3 mm, about 4 mm, about 5 mm, about 6 mm, about 7 mm, about 8 mm, about 9 mm, or about 10 mm.

The posterior portion width P, anterior portion width A, first lateral side width L, and second lateral side width L' may have the same size relative to each other, or may have a different size relative to each other. When the position of the vertical aperture 60, 160, 160a, 260, and 360 is positioned toward the anterior portion 40, 140, 140a, 240, and 340, the anterior portion width A decreases and the posterior portion width increases, relative to a comparable implant 1, 101, 101a, 201, and 301 in which the vertical aperture 60, 160, 160a, 260, and 360 is centered, and vice versa. When the position of the vertical aperture 60, 160, 160a, 260, and 360 is positioned toward a lateral side 30, 130, 130a, 230, and 330, the first lateral side width L (e.g., the side to which the vertical aperture 60, 160, 160a, 260, and 360 is positioned closest) decreases and the second lateral side width increases, relative to a comparable implant 1, 101, 101a, 201, and 301 in which the vertical aperture 60, 160, 160a, 260, and 360 is centered, and vice versa. The same holds true with respect to the positioning of the integration plate vertical aperture 61, 161, 161a, 261, and 361.

The posterior portion width P, anterior portion width A, and/or first and second lateral side width L and L' may allow for better stress sharing between the implant 1, 101, 101a, 201, and 301 and the adjacent vertebral endplates, and helps to compensate for the weaker posterior endplate bone. In some aspects, the transverse rim 100, 200, 200a, 300, and 400 has a generally large surface area and contacts the vertebral endplate. The transverse rim 100, 200, 200a, 300, and 400 may act to better distribute contact stresses upon the implant 1, 101, 101a, 201, and 301, and minimize the risk of subsidence while maximizing contact with the apophyseal supportive bone. Some studies have challenged the characterization of the posterior endplate bone as weaker.

The size and shape of the vertical aperture 60, 160, 160a, 260, and 360, as well as the integration plate vertical aperture 61, 161, 161a, 261, and 361 are carefully chosen to achieve a preferable design tradeoff for the particular application envisioned for the implant 1, 101, 101a, 201, and 301. The vertical aperture 60, 160, 160a, 260, and 360 or integration plate vertical aperture 61, 161, 161a, 261, and 361 preferably maximizes the surface area of the top surface 10, 110, 110a, 210, and 310, integration plate top surface 81, 181, 181a, 281, and 381, and/or bottom surface 20, 120, 120a, 220, and 320, while at the same time maximizing both the capacity for radiographic visualization and access to the bone graft material. It is highly preferred that the bone graft material bear at least some of the load forces of the spine once the implant 1, 101, 101a, 201, and 301 is implanted. The size, shape, and location of the vertical aperture 60, 160, 160a, 260, and 360 or integration plate vertical aperture 61, 161, 161a, 261, and 361 are predetermined by the application to which the implant 1, 101, 101a, 201, and 301 will be used, as well as the vertebrae between which the implant 1, 101, 101a, 201, and 301 will be implanted, as well as the particular location in the intervertebral space in which the implant 1, 101, 101a, 201, and 301 will be implanted.

The vertical aperture 60, 160, 160a, 260, and 360, and the integration plate vertical aperture 61, 161, 161a, 261, and 361 each preferably comprises a maximum width at its center. The width of the vertical aperture 60, 160, 160a, 260, and 360, and the integration plate vertical aperture 61, 161, 161a, 261, and 361 may range from about 20% to about 80% of the distance between opposing lateral sides. In some aspects, the width ranges from about 40% to about 80% of the distance between the opposing lateral sides. In some aspects, the width ranges from about 50% to about 70% of the distance between the opposing lateral sides. In some aspects, the width ranges from about 50% to about 65% of the distance between the opposing lateral sides. In some aspects, the width ranges from about 60% to about 70% of the distance between the opposing lateral sides. In some aspects, the width ranges from about 55% to about 75% of the distance between the opposing lateral sides. In some aspects, the width ranges from about 60% to about 80% of the distance between the opposing lateral sides. In some aspects, the width is about 40%, about 45%, about 50%, about 55%, about 60%, about 65%, about 70%, about 75%, about 80%, about 85%, or about 90% of the distance between the opposing lateral sides. Preferably, the width of the vertical aperture 60, 160, 160a, 260, and 360, or the integration plate vertical aperture 61, 161, 161a, 261, and 361 comprises the dimension between the lateral sides.

The length of the vertical aperture 60, 160, 160a, 260, and 360, and the integration plate vertical aperture 61, 161, 161a, 261, and 361 may range from about 20% to about 80% of the distance between the anterior and posterior edges. In some aspects, the length ranges from about 40% to about 80% of the distance between the anterior and posterior edges. In some aspects, the length ranges from about 50% to about 70% of the distance between the anterior and posterior edges. In some aspects, the length ranges from about 50% to about 65% of the distance between the anterior and posterior edges. In some aspects, the length ranges from about 60% to about 70% of the distance between the anterior and posterior edges. In some aspects, the length ranges from about 55% to about 75% of the distance between the anterior and posterior edges. In some aspects, the length ranges from about 60% to about 80% of the distance between the anterior and posterior edges. In some aspects, the length is about 40%, about 45%, about 50%, about 55%, about 60%, about 65%, about 70%, about 75%, about 80%, about 85%, or about 90% of the distance between the anterior and posterior edges. Preferably, the length of the vertical aperture 60, 160, 160*a*, 260, and 360, or the integration plate vertical aperture 61, 161, 161*a*, 261, and 361 comprises the dimension between the anterior and posterior edges. The size of the length and the size of the width of the vertical aperture 60, 160, 160*a*, 260, and 360, or the integration plate vertical aperture 61, 161, 161*a*, 261, and 361 may vary independently of each other.

The drawings show examples different possible sizes, shapes, and positions of the vertical aperture 60, 160, 160*a*, 260, and 360 and integration plate vertical aperture 61, 161, 161*a*, 261, and 361. The drawings simply illustrate various configurations, and are not to be considered limiting in any way.

Figure 15A:
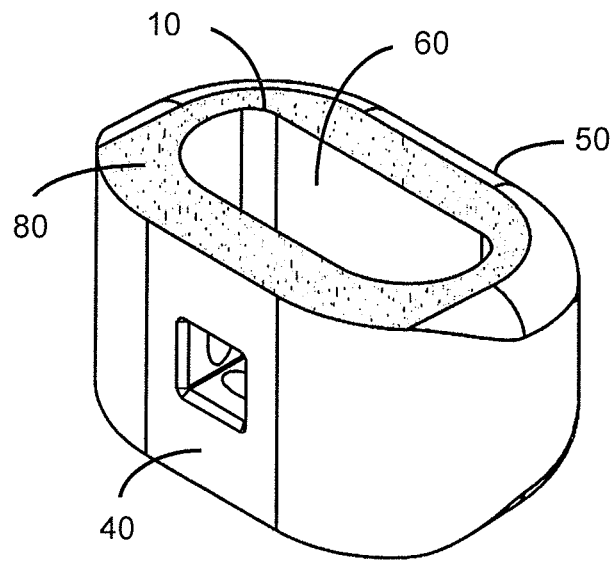
FIG. 15A shows a perspective view of an enlarged vertical aperture on an implant.
Figure 15B:
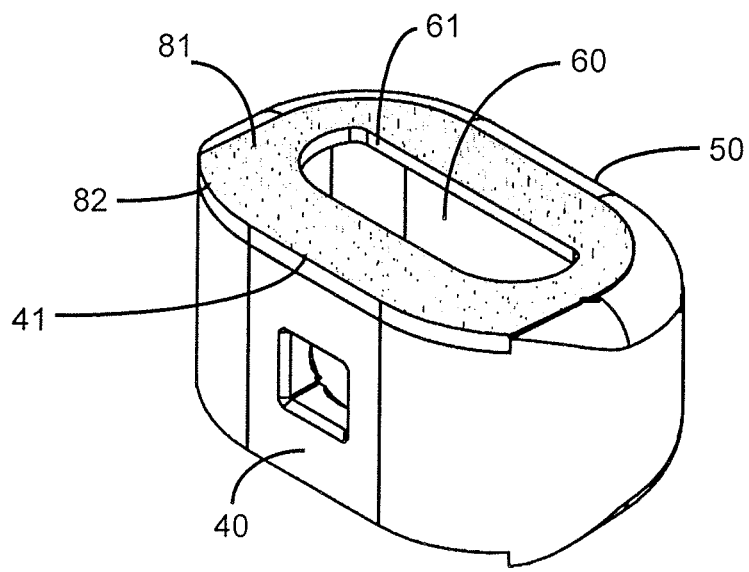
FIG. 15B shows a perspective view of an enlarged vertical aperture through an integration plate.

FIG. 15A shows the vertical aperture 60 and the top surface 10 of the implant 1, and FIG. 15B shows the vertical aperture 61 and the top surface 81 of the integration plate 82. The vertical aperture 60, 61 may comprise any suitable shape, dimensions, and position on the implant 1. For example, FIG. 16A shows the vertical aperture 60, 61 substantially in the center of the implant 1. FIG. 16B shows the vertical aperture 60, 61 with a wider length and width such that the posterior portion width P, anterior portion width A, first lateral side width L, and second lateral side width L' are diminished relative to the embodiment shown in FIG. 16A. FIG. 16C shows an example of the vertical aperture 60, 61 positioned to a lateral side of the implant 1. FIG. 16D shows an example of the vertical aperture 60, 61 having a wider length and width, and positioned nearer to the anterior portion 40 of the implant 1.

Figure 17A:
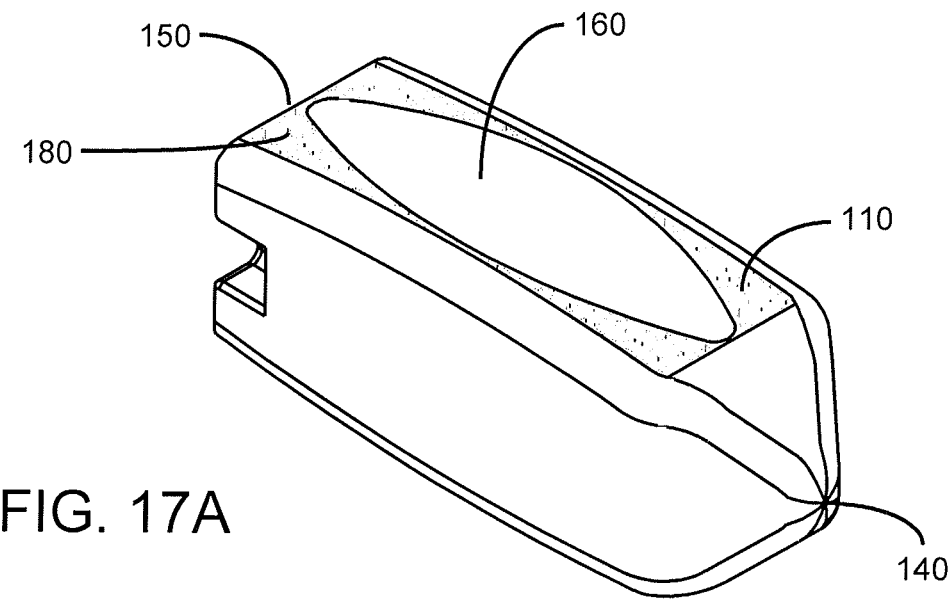
FIG. 17A shows a perspective view of an enlarged vertical aperture on another embodiment of an implant.
Figure 17B:
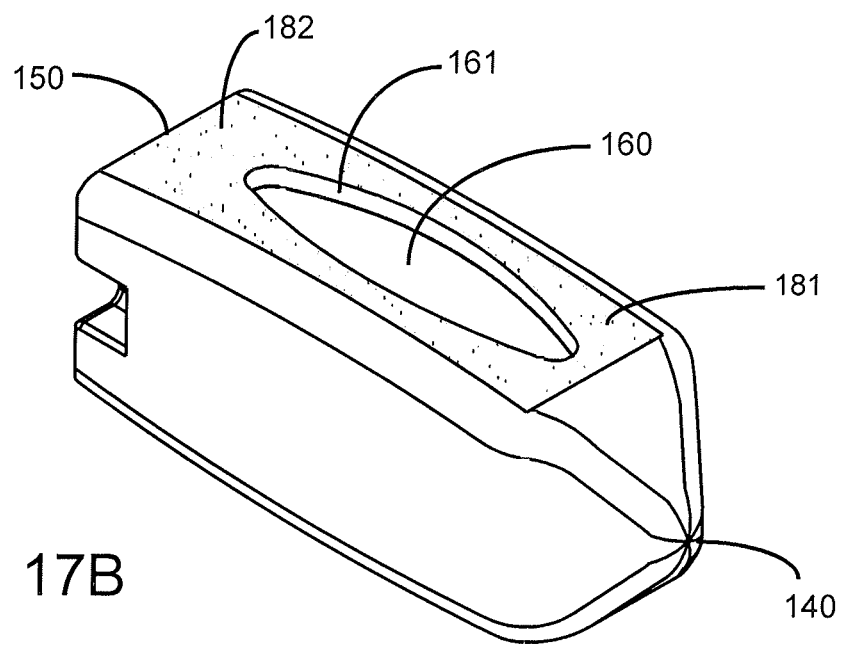
FIG. 17B shows a perspective view of an enlarged vertical aperture through an integration plate on another embodiment of an implant.
Figure 18A:
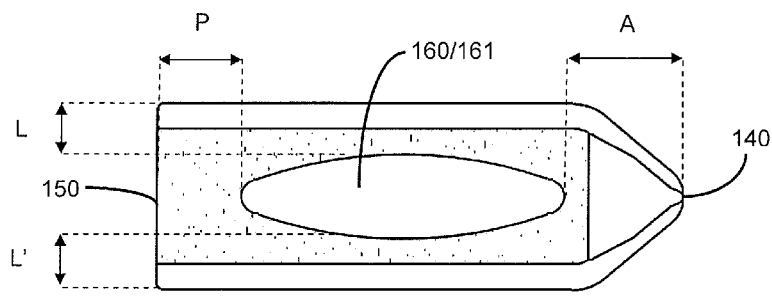
FIG. 18A shows a top view of an embodiment of a vertical aperture for the implant of FIG. 17.
Figure 18B:
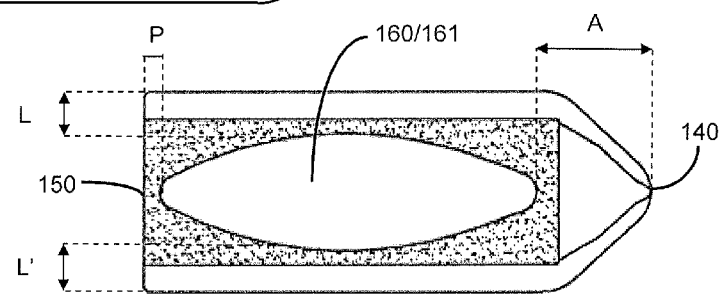
FIG. 18B shows a top view of another embodiment of a vertical aperture for the implant of FIG. 17.
Figure 18C:
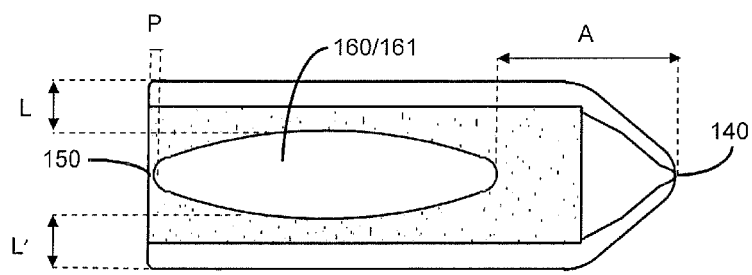
FIG. 18C shows a top view of another embodiment of a vertical aperture for the implant of FIG. 17.
Figure 18D:
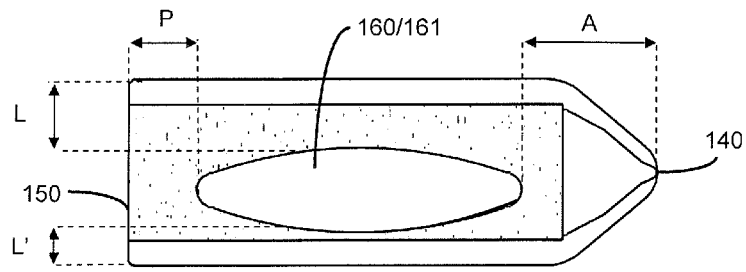
FIG. 18D shows a top view of another embodiment of a vertical aperture for the implant of FIG. 17.
Figure 19A:
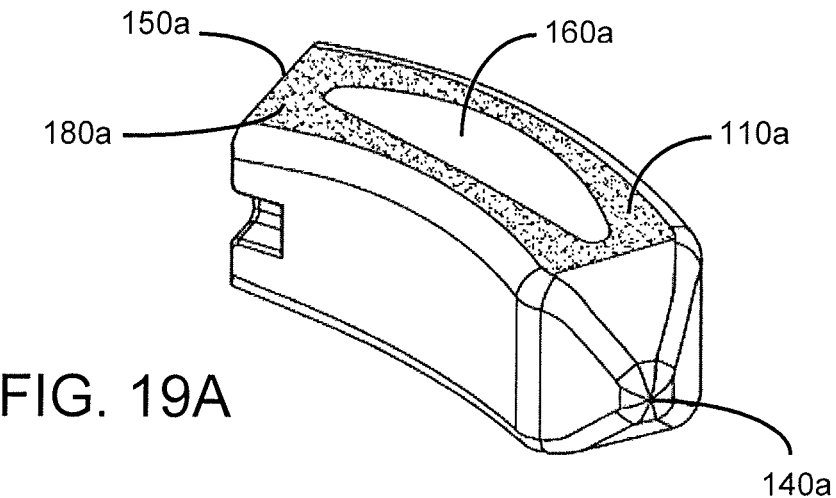
FIG. 19A shows a perspective view of an enlarged vertical aperture on another embodiment of an implant.
Figure 19B:
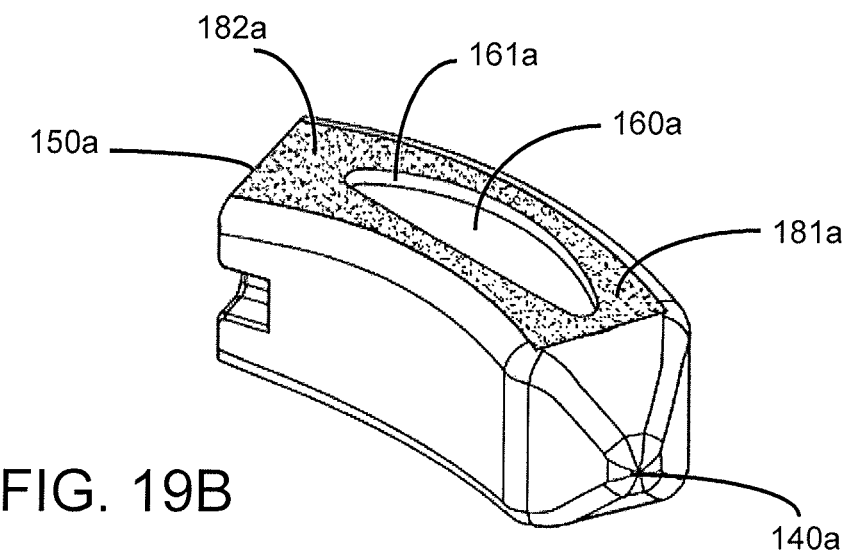
FIG. 19B shows a perspective view of an enlarged vertical aperture through an integration plate on another embodiment of an implant.

FIG. 17A shows the vertical aperture 160 and the top surface 110 of the implant 101, and FIG. 17B shows the vertical aperture 161 and the top surface 181 of the integration plate 182. As shown, the length and width of the vertical aperture 160 may be enlarged such that the vertical aperture 160 spans most of the surface area of the top surface 110 (FIG. 17A), or the vertical aperture 161 may be positioned toward the anterior portion 140 (FIG. 17B). Such configurations, in addition to other possible configurations, are shown from a top perspective in FIGS. 18A-18D. For example, FIG. 18A shows the vertical aperture 160, 161 substantially in the center of the implant 101, though the anterior-most edge of the aperture 160, 161 is positioned more toward the anterior edge of the roughened surface topography 180 of the top surface 110. FIG. 18B shows the enlarged vertical aperture 160, 161 that is also positioned nearer to the posterior portion 150. FIG. 18C shows a vertical aperture 160, 161 having a smaller profile that is positioned proximate to the posterior portion 150. FIG. 18D shows a vertical aperture 160, 161 having a smaller profile that is positioned nearer to the a lateral side 130.

Similar to the embodiments shown in FIGS. 17 and 18, FIGS. 19 and 20 illustrate different shapes and dimensions of the vertical aperture 160*a* and 161*a* of the implant 101*a*. For example, FIG. 19A shows the vertical aperture 160*a* and the top surface 110*a* of the implant 101*a*, and FIG. 19B shows the vertical aperture 161*a* and the top surface 181*a* of the integration plate 182*a*. Although the implant 101*a* curves, and the vertical aperture 160*a* and 161*a* has curved edges as well, it is not necessary the outer arc of the implant 101*a* curve and aperture 160*a* and 161*a* lateral curves are identical. The shape of the implant 101*a* and the shape of the vertical aperture 160*a* and 161*a* may be independent of each other.

Figure 20A:
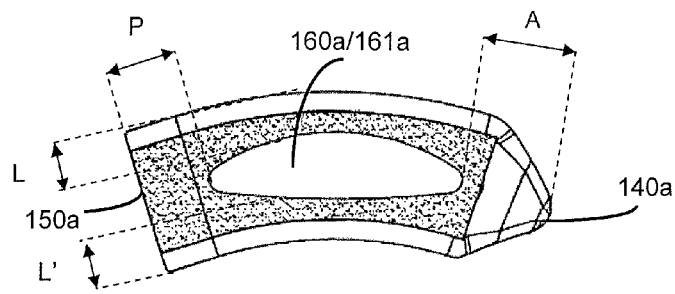
FIG. 20A shows a top view of an embodiment of a vertical aperture for the implant of FIG. 19.
Figure 20B:
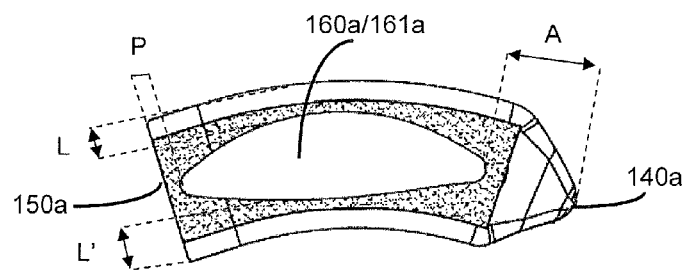
FIG. 20B shows a top view of another embodiment of a vertical aperture for the implant of FIG. 19.
Figure 20C:
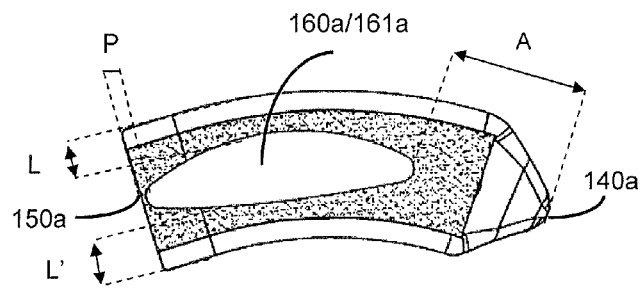
FIG. 20C shows a top view of another embodiment of a vertical aperture for the implant of FIG. 19.
Figure 20D:
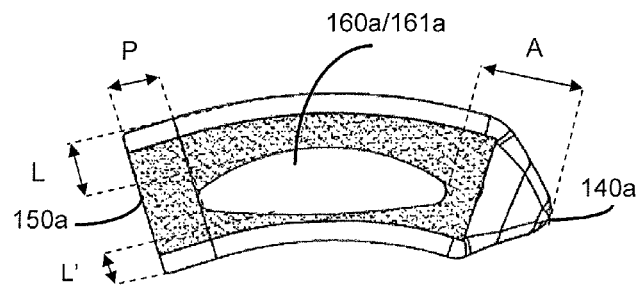
FIG. 20D shows a top view of another embodiment of a vertical aperture for the implant of FIG. 19.

FIG. 20A shows the vertical aperture 160*a*, 161*a* substantially in the center of the implant 101*a*, though the anterior-most edge of the aperture 160*a*, 161*a* is positioned more toward the anterior edge of the roughened surface topography 180*a* of the top surface 110*a*. FIG. 20B shows the enlarged vertical aperture 160*a*, 161*a* that is also positioned nearer to the posterior portion 150*a*. FIG. 20C shows a vertical aperture 160*a*, 161*a* having a smaller profile that is positioned proximate to the posterior portion 150*a*. FIG. 20D shows a vertical aperture 160*a*, 161*a* having a smaller profile that is positioned nearer to the a lateral side 130*a*.

Figure 21A:
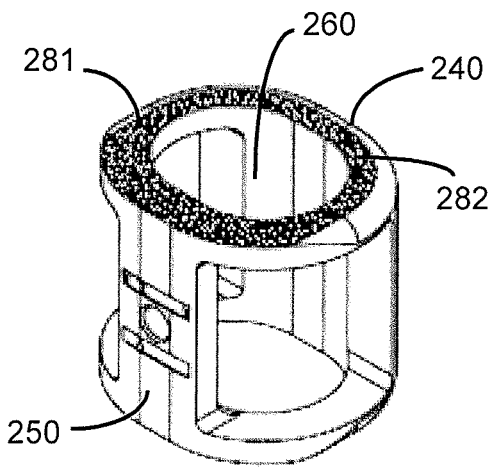
FIG. 21A shows a perspective view of an enlarged vertical aperture on another embodiment of an implant.
Figure 21B:
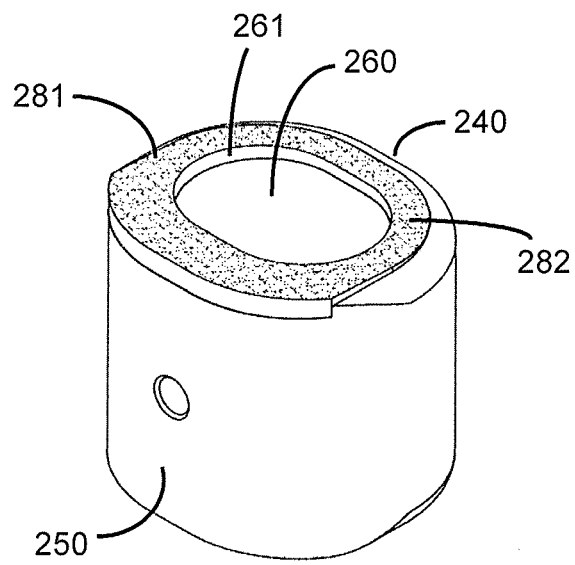
FIG. 21B shows a perspective view of an enlarged vertical aperture through an integration plate on another embodiment of an implant.
Figure 22A:
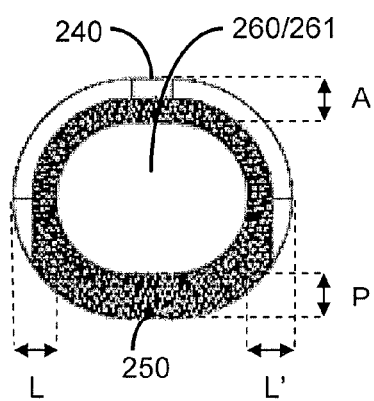
FIG. 22A shows a top view of an embodiment of a vertical aperture for the implant of FIG. 21.
Figure 22B:
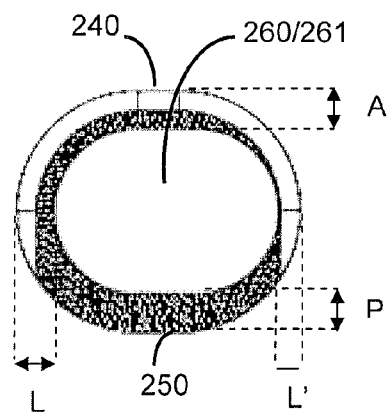
FIG. 22B shows a top view of another embodiment of a vertical aperture for the implant of FIG. 21.
Figure 22C:
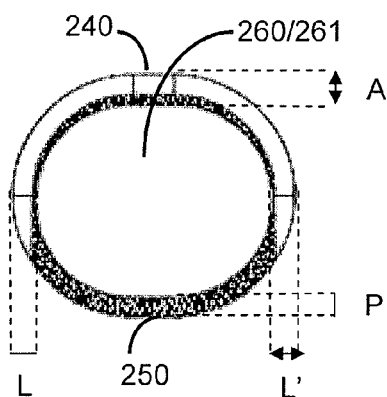
FIG. 22C shows a top view of another embodiment of a vertical aperture for the implant of FIG. 21.
Figure 22D:
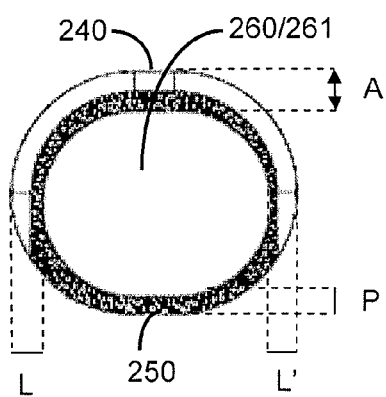
FIG. 22D shows a top view of another embodiment of a vertical aperture for the implant of FIG. 21.

FIG. 21A shows an embodiment of the implant 201 and its vertical aperture 260 and top surface 210, and FIG. 21B shows the vertical aperture 261 and the top surface 281 of the integration plate 282. FIG. 22A shows the vertical aperture 260, 261 substantially in the center of the implant 201. FIG. 22B shows the vertical aperture 260, 261 positioned nearer to the second lateral side. FIG. 22C shows a wider vertical aperture 260, 261 positioned substantially in the center of the implant 201. FIG. 22D shows the vertical aperture 260, 261 positioned nearer to the posterior portion 250.

Figure 23A:
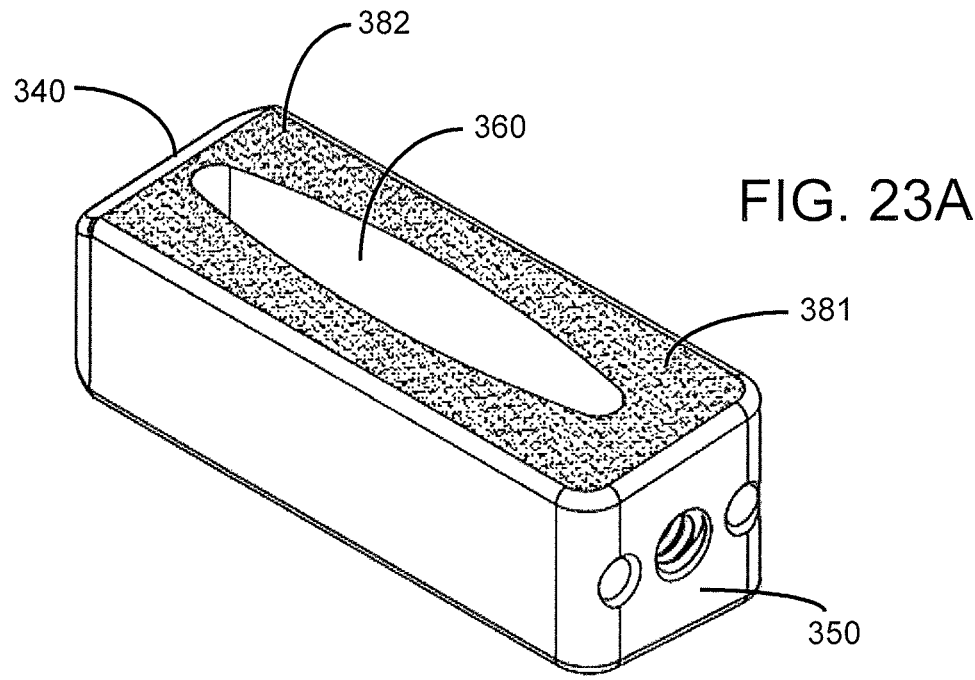
FIG. 23A shows a perspective view of an enlarged vertical aperture on another embodiment of an implant.
Figure 23B:
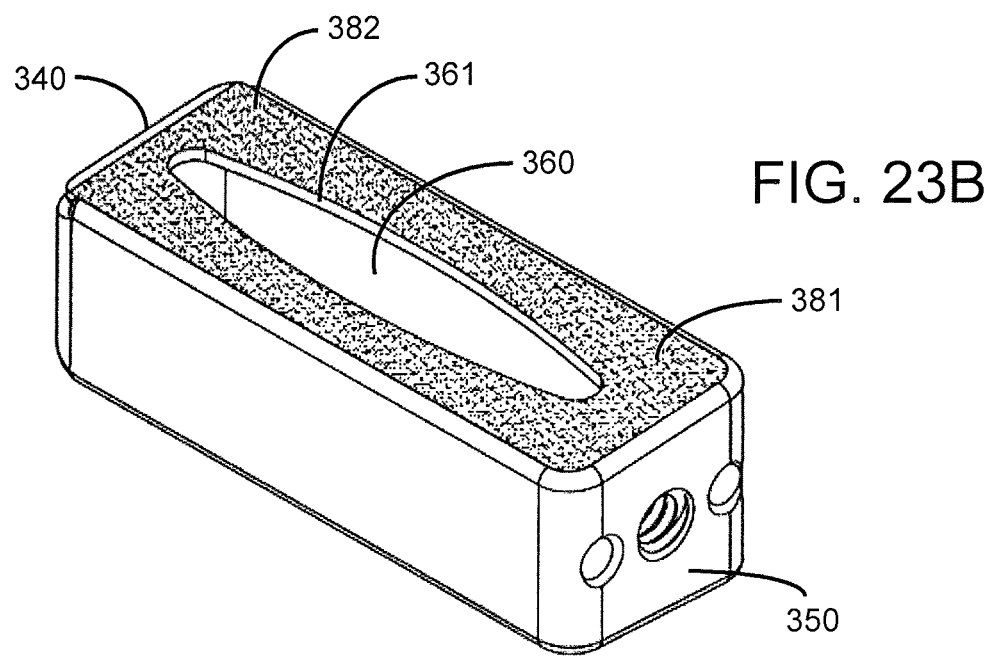
FIG. 23B shows a perspective view of an enlarged vertical aperture through an integration plate on another embodiment of an implant.
Figure 24A:
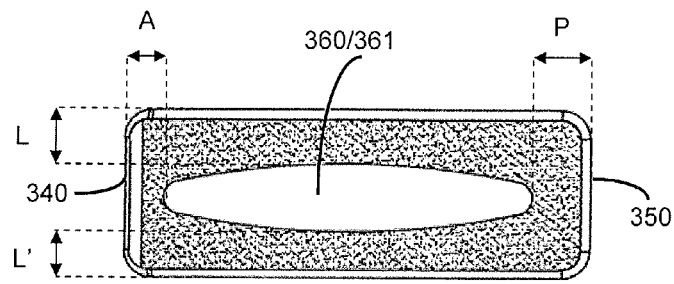
FIG. 24A shows a top view of an embodiment of a vertical aperture for the implant of FIG. 23.
Figure 24B:
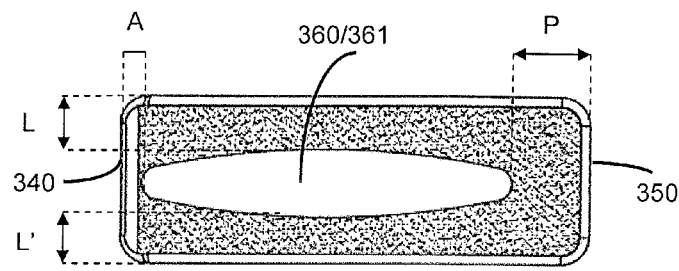
FIG. 24B shows a top view of another embodiment of a vertical aperture for the implant of FIG. 23.
Figure 24C:
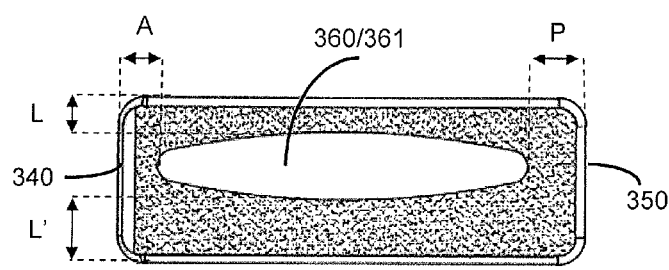
FIG. 24C shows a top view of another embodiment of a vertical aperture for the implant of FIG. 23.
Figure 24D:
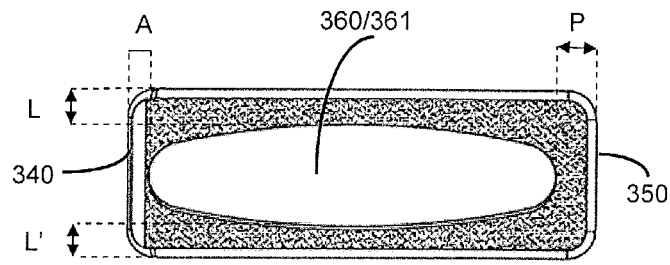
FIG. 24D shows a top view of another embodiment of a vertical aperture for the implant of FIG. 23.

FIG. 23A shows the vertical aperture 360 and the top surface 310 of the implant 301, and FIG. 23B shows the vertical aperture 361 and the top surface 381 of the integration plate 382. As shown, the vertical aperture 360 and 361 is positioned substantially in the center of the implant 301. The centered configuration is shown from a top perspective in FIG. 24A. FIG. 24B shows the vertical aperture 360, 361 positioned nearer to the anterior portion 350. FIG. 24C shows the vertical aperture 360, 361 positioned proximate to a lateral side 330. FIG. 24D shows an enlarged vertical aperture 360, 361 positioned substantially in the center of the implant 301.

Example Surgical Methods

The following examples of surgical methods are included to more clearly demonstrate the overall nature of the invention. These examples are exemplary, not restrictive, of the invention.

Certain embodiments of the invention are particularly suited for use during interbody spinal implant procedures currently known in the art. For example, the disc space may be accessed using a standard mini open retroperitoneal laparotomy approach. The center of the disc space is located by AP fluoroscopy taking care to make sure the pedicles are equidistant from the spinous process. The disc space is then incised by making a window in the annulus for insertion of certain embodiments of the spinal implant 1 (a 32 or 36 mm window in the annulus is typically suitable for insertion). The process according to the invention minimizes, if it does not eliminate, the cutting of bone. The endplates are cleaned of all cartilage with a curette, however, and a size-specific rasp (or broach) may then be used.

Use of a rasp preferably substantially minimizes or eliminates removal of bone, thus substantially minimizing or eliminating impact to the natural anatomical arch, or concavity, of the vertebral endplate while preserving much of the apophyseal rim. Preservation of the anatomical concavity is particularly advantageous in maintaining biomechanical integrity of the spine. For example, in a healthy spine, the transfer of compressive loads from the vertebrae to the spinal disc is achieved via hoop stresses acting upon the natural arch of the endplate. The distribution of forces, and resultant hoop stress, along the natural arch allows the relatively thin shell of subchondral bone to transfer large amounts of load.

During traditional fusion procedures, the vertebral endplate natural arch may be significantly removed due to excessive surface preparation for implant placement and seating. This is especially common where the implant is to be seated near the center of the vertebral endplate or the implant is of relatively small medial-lateral width. Breaching the vertebral endplate natural arch disrupts the biomechanical integrity of the vertebral endplate such that shear stress, rather than hoop stress, acts upon the endplate surface. This redistribution of stresses may result in subsidence of the implant into the vertebral body.

Preferred embodiments of the surgical method minimize endplate bone removal on the whole, while still allowing for some removal along the vertebral endplate far lateral edges where the subchondral bone is thickest. Still further, certain embodiments of the interbody spinal implant 1, 101, 101a, 201, and 301 include smooth, rounded, and highly radiused posterior portions and lateral sides which may minimize extraneous bone removal for endplate preparation and reduce localized stress concentrations. Thus, interbody surgical implant 1, 101, 101a, 201, and 301 and methods of using it are particularly useful in preserving the natural arch of the vertebral endplate and minimizing the chance of implant subsidence.

Because the endplates are spared during the process of inserting the spinal implant 1, 101, 101a, 201, and 301, hoop stress of the inferior and superior endplates is maintained. Spared endplates allow the transfer of axial stress to the apophasis. Endplate flexion allows the bone graft placed in the interior of the spinal implant 1 to accept and share stress transmitted from the endplates. In addition, spared endplates minimize the concern that BMP might erode the cancellous bone.

Certain embodiments of the interbody spinal implant 1, 101, 101a, 201, and 301 may maintain a position between the vertebral endplates due, at least in part, to resultant annular tension attributable to press-fit surgical implantation and, post-operatively, improved osteointegration at the top surface 10, 110, 110a, 210, and 310; the bottom surface 20, 120, 120a, 220, and 320; or both surfaces.

Surgical implants and methods tension the vertebral annulus via distraction. These embodiments and methods may also restore spinal lordosis, thus improving sagittal and coronal alignment. Implant systems currently known in the art require additional instrumentation, such as distraction plugs, to tension the annulus. These distraction plugs require further tertiary instrumentation, however, to maintain the lordotic correction during actual spinal implant insertion. If tertiary instrumentation is not used, then some amount of lordotic correction may be lost upon distraction plug removal. Interbody spinal implant 1, according to certain embodiments of the invention, is particularly advantageous in improving spinal lordosis without the need for tertiary instrumentation, thus reducing the instrument load upon the surgeon. This reduced instrument load may further decrease the complexity, and required steps, of the implantation procedure.

Certain embodiments of the spinal implant 1, 101, 101a, 201, and 301 may also reduce deformities (such as isthmic spondylolythesis) caused by distraction implant methods. Traditional implant systems require secondary or additional instrumentation to maintain the relative position of the vertebrae or distract collapsed disc spaces. In contrast, interbody spinal implant 1, 101, 101a, 201, and 301 may be used as the final distractor and thus maintain the relative position of the vertebrae without the need for secondary instrumentation.

Certain embodiments collectively comprise a family of implants, each having a common design philosophy. These implants and the associated surgical technique have been designed to address at least the ten, separate challenges associated with the current generation of traditional anterior spinal fusion devices listed above in the Background section of this document.

Embodiments of the invention allow end-plate preparation with custom-designed rasps. These rasps preferably have a geometry matched with the geometry of the implant. The rasps conveniently remove cartilage from the endplates and remove minimal bone, only in the postero-lateral regions of the vertebral end-plates. It has been reported in the literature that the end-plate is the strongest in postero-lateral regions.

After desired annulotomy and discectomy, embodiments of the invention first adequately distract the disc space by inserting (through impaction) and removing sequentially larger sizes of very smooth distractors, which have been size matched with the size of the available implant 1, 101, 101a, 201, and 301. Once adequate distraction is achieved, the surgeon prepares the end-plate with a rasp. There is no secondary instrumentation required to keep the disc space distracted while the implant 1, 101, 101a, 201, and 301 is inserted, as the implant 1, 101, 101a, 201, and 301 has sufficient mechanical strength that it is impacted into the disc space. In fact, the height of the implant 1, 101, 101a, 201, and 301 is preferably about 1 mm greater than the height of the rasp used for end-plate preparation, to create some additional tension in the annulus by implantation, which creates a stable implant construct in the disc space.

The implant geometry has features which allow it to be implanted via any one of an anterior, antero-lateral, or lateral approach, providing tremendous intra-operative flexibility of options. The implant 1, 101, 101a, 201, and 301 has adequate strength to allow impact. The sides of the implant 1, 101, 101a, 201, and 301 have smooth surfaces to allow for easy implantation and, specifically, to prevent binding of the implant 1, 101, 101a, 201, and 301 to soft tissues during implantation.

The invention encompasses a number of different implant 1, 101, 101a, 201, and 301 configurations, including a one-piece, titanium-only implant and a composite implant formed of top and bottom plates (components) made out of titanium. The surfaces exposed to the vertebral body are dual acid etched to allow for bony in-growth over time, and to provide resistance against expulsion. The top and bottom titanium plates are assembled together with the implant body that is injection molded with PEEK. The net result is a composite implant that has engineered stiffness for its clinical application.

It is believed that an intact vertebral end-plate deflects like a diaphragm under axial compressive loads generated due to physiologic activities. If a spinal fusion implant is inserted in the prepared disc space via a procedure which does not destroy the end-plates, and if the implant contacts the end-plates only peripherally, the central dome of the end-plates can still deflect under physiologic loads. This deflection of the dome can pressurize the bone graft material packed inside the spinal implant, hence allowing it to heal naturally. The implant 1, 101, 101a, 201, and 301 designed according to certain embodiments allows the vertebral end-plate to deflect and allows healing of the bone graft into fusion.

The roughened topography 80, 180, 180a, 280, and 380 whether directly on the top/bottom surface of the implant 1, 101, 101a, 201, and 301 or the integration plate 82, 182, 182a, 282, and 382 reacts with contacting bone to promote biologic activities that facilitate fusion of bone to the implant 1, 101, 101a, 201, and 301.

The implant 1, 101, 101a, 201, and 301 may comprise a lordotic angle L, e.g., may be wedge-shaped to facilitate sagittal alignment. Thus, for example, the anterior portion 40, 140, 140a, 240, and 340 of the implant 1, 101, 101a, 201, and 301 may comprise a height that is larger than the height of the posterior portion 50, 150, 150a, 250, and 350. The lordotic angle L may be established by the implant 1, 101, 101a, 201, and 301 itself, or may be established by the integration plate 82, 182, 182a, 282, and 382 when combined with the implant 1, 101, 101a, 201, and 301.

The lordotic angle L of the implant 1 preferably closely approximates, or otherwise is substantially the same as, the angle of lordosis of the spine of the patient where the implant 1, 101, 101a, 201, and 301 will be implanted. In some aspects, the integration plate 82, 182, 182a, 282, and 382 increases the lordotic angle L by about 3% to about 5%, measured according to the angle of lordosis of a particular patient's spine.

The implant 1, 101, 101a, 201, and 301 may have a lordotic angle L about 3%, about 3.3%, about 3.5%, about 3.7%, about 4%, about 4.3%, about 4.5%, about 4.7%, or about 5% greater than the patient's angle of lordosis, though percentages greater than 5% or lesser 3% are possible. The increase of about 3% to about 5% preferably results from the combination of the protruding height of the integration plate 82, 182, 182a, 282, and 382 on the top portion 10, 110, 110a, 210, and 310 and bottom portion 20, 120, 120a, 220, and 320 of the implant 1, 101, 101a, 201, and 301.

The expulsion-resistant edge 8, 108, 108a, 208, and 308 may comprise an anti-expulsion edge angle E. The anti-expulsion edge angle E may be from about 80 degrees to about 100 degrees. In preferred aspects, the anti-expulsion edge angle E may be measured by taking into account the lordosis angle L of the implant 1, 101, 101a, 201, and 301. In highly preferred aspects, the anti-expulsion edge angle E is measured by subtracting half of the lordotic angle L from 90 degrees. For example, where the lordosis angle L of the implant 1, 101, 101a, 201, and 301 is 12 degrees, the anti-expulsion edge angle E is 84 degrees (90−(12×0.5)). The anti-expulsion edge angle E may be about 80 degrees, about 81 degrees, about 82 degrees, about 83 degrees, about 84 degrees, about 85 degrees, about 86 degrees, about 86.5 degrees, about 87 degrees, about 88 degrees, or about 89 degrees.

The top and bottom surfaces of the implant may be made out of titanium and are dual acid etched. The dual acid etching process creates a highly roughened texture on these surfaces, which generates tremendous resistance to expulsion. The width of these dual acid etched surfaces is very broad and creates a large area of contact with the vertebral end-plates, further increasing the resistance to expulsion.

The implant 1, 101, 101a, 201, and 301 according to certain embodiments of the invention has a large foot-print, and offers several sizes. Because there is no secondary instrument required to maintain distraction during implantation, all the medial-lateral (ML) exposure is available as implantable ML width of the implant 1, 101, 101a, 201, and 301. This feature allows the implant 1, 101, 101a, 201, and 301 to contact the vertebral end-plates at the peripheral apophyseal rim, where the end-plates are the strongest and least likely to subside.

Further, there are no teeth on the top and bottom surfaces (teeth can create stress risers in the end-plate, encouraging subsidence). Except for certain faces, all the implant surfaces have heavily rounded edges, creating a low stress contact with the end-plates. The wide rim of the top and bottom surfaces, in contact with the end-plates, creates a low-stress contact due to the large surface area. Finally, the implant construct has an engineered stiffness to minimize the stiffness mismatch with the vertebral body which it contacts.

Even the titanium-only embodiment of the invention has been designed with large windows to allow for radiographic evaluation of fusion, both through AP and lateral X-rays. A composite implant minimizes the volume of titanium, and localizes it to the top and bottom surfaces. The rest of the implant is made of PEEK which is radiolucent and allows for free radiographic visualization.

Although illustrated and described above with reference to certain specific embodiments and examples, the invention is nevertheless not intended to be limited to the details shown. Rather, various modifications may be made in the details within the scope and range of equivalents of the claims and without departing from the spirit of the invention. It is expressly intended, for example, that all ranges broadly recited in this document include within their scope all narrower ranges which fall within the broader ranges. In addition, features of one embodiment may be incorporated into another embodiment.

What is claimed:

1. An interbody spinal implant, comprising:
a body having a top surface, a bottom surface, opposing lateral sides, opposing anterior and posterior portions, a substantially hollow center, and a single vertical aperture extending from the top surface to the bottom surface;
wherein the single vertical aperture has a size and shape for both maximizing the surface area of the top surface and the bottom surface available for contacting vertebral endplate bone and maximizing the contact of a bone graft material disposed in the substantially hollow center and in the aperture with vertebral endplate bone, defines a transverse rim on the top surface and on the bottom surface, the transverse rim comprising an anterior portion width, a posterior portion width, a first lateral side width, and a second lateral side width, and has a maximum width at its center ranging from about 40% to about 80% of the distance between the opposing lateral sides and tapering inwardly from the center to each of its ends, one end proximate the anterior portion and the other end proximate the posterior portion, wherein the anterior portion width is different from the posterior portion width or the first lateral side width is different from the second lateral side width;
the body having a roughened bioactive surface topography, without teeth, on at least a portion of the top surface, the bottom surface, or both the top and bottom surfaces adapted to grip bone and inhibit migration of the implant;
the body having generally rounded and blunt intersections defined along the entire lengths between the top surface and the lateral sides, the bottom surface and the lateral sides, and either the top surface and the posterior portion and the bottom surface and the posterior portion, or the top surface and the anterior portion and the bottom surface and the anterior portion; and
the body having at least one sharp edge between the top and bottom surfaces and the anterior portion or the top and bottom surfaces and the posterior portion.

2. The interbody spinal implant of claim 1, wherein the body is comprised of a metal.

3. The interbody spinal implant of claim 1, wherein the body is comprised of a non-metal polymer.

4. The interbody spinal implant of claim 1, wherein the body is comprised of a composite of a metal and a non-metal polymer selected from the group consisting of polyetheretherketone, hedrocel, and ultra-high molecular weight polyethylene.

5. The interbody spinal implant of claim 1, further comprising bone graft material disposed in the substantially hollow center of the body and in the vertical aperture, and adapted to facilitate the formation of a solid fusion column within the spine.

6. The interbody spinal implant of claim 5, wherein the bone graft material is cancellous autograft bone, allograft bone, demineralized bone matrix (DBM), porous synthetic bone graft substitute, bone morphogenic protein (BMP), or a combination thereof.

7. The interbody spinal implant of claim 1, wherein the anterior portion width of the rim is less than the posterior portion width of the rim.

8. The interbody spinal implant of claim 1, wherein the posterior portion width of the rim is less than the anterior portion width of the rim.

9. The interbody spinal implant of claim 1, wherein the first lateral side width of the rim is less than the second lateral side width of the rim.

10. The interbody spinal implant of claim 1, wherein the maximum width at the center of the vertical aperture ranges from about 50% to about 65% of the distance between the opposing lateral sides.

11. The interbody spinal implant of claim 1, wherein the top surface and the bottom surface have a roughened bioactive surface topography adapted to grip bone and inhibit migration of the implant.

12. The interbody spinal implant of claim 1, further comprising a lordotic angle adapted to facilitate alignment of the spine.

13. An interbody spinal implant, comprising:
a body having a top surface, a bottom surface, opposing lateral sides, opposing anterior and posterior portions, a substantially hollow center, and a single vertical aperture extending from the top surface to the bottom surface;
wherein the body has generally rounded and blunt intersections defined along the entire lengths between the top surface and the lateral sides, the bottom surface and the lateral sides, and either the top surface and the posterior portion and the bottom surface and the posterior portion, or the top surface and the anterior portion and the bottom surface and the anterior portion;
a first integration plate having a top surface, a bottom surface, opposing lateral sides, opposing anterior and posterior portions, and a single vertical aperture extending from the top surface to the bottom surface and aligning with the single vertical aperture of the body;
optionally, a second integration plate having a top surface, a bottom surface, opposing lateral sides, opposing anterior and posterior portions, and a single vertical aperture extending from the top surface to the bottom surface and aligning with the single vertical aperture of the body;
wherein the single vertical aperture of the first integration plate has a size and shape for both maximizing the surface area of the top surface of the first integration plate available for contacting vertebral endplate bone and maximizing the contact of a bone graft material disposed in the substantially hollow center and in the single vertical aperture of the first integration plate with vertebral endplate bone, defines a transverse rim on the top surface of the first integration plate, the rim comprising an anterior portion width, a posterior portion width, a first lateral side width, and a second lateral side width, and has a maximum width at its center ranging from about 40% to about 80% of the distance between the opposing lateral sides of the first integration plate and tapering inwardly from the center to each of its ends, one end proximate the anterior portion and the other end proximate the posterior portion, wherein the anterior portion width is different from the posterior portion width or the first lateral side width is different from the second lateral side width;
the first integration plate having a roughened bioactive surface topography, without teeth, on the top surface adapted to grip bone and inhibit migration of the implant;
the first integration plate having at least one sharp edge between the top surface and the anterior portion or the top surface and the posterior portion; and
wherein the single vertical aperture of the second integration plate has a size and shape for both maximizing the surface area of the top surface of the second integration plate available for contacting vertebral endplate bone and maximizing the contact of a bone graft material disposed in the substantially hollow center and in the single vertical aperture of the second integration plate with vertebral endplate bone, defines a transverse rim on the top surface of the second integration plate, the rim comprising an anterior portion width, a posterior portion width, a first lateral side width, and a second lateral side width, and has a maximum width at its center ranging from about 40% to about 80% of the distance between the opposing lateral sides of the second integration plate, wherein the anterior portion width is different from the posterior portion width or the first lateral side width is different from the second lateral side width, the single vertical aperture of the optional second integration plate having a maximum width at its center, between the opposing lateral sides, and tapering inwardly from the center to each of its ends, one end proximate the anterior portion and the other end proximate the posterior portion;
the optional second integration plate having a roughened bioactive surface topography, without teeth, on the top surface adapted to grip bone and inhibit migration of the implant; and
the optional second integration plate having at least one sharp edge between the top surface and the anterior portion or the top surface and the posterior portion.

14. The interbody spinal implant of claim 13, wherein the body, the first integration plate, and the optional second integration plate are each comprised of a metal.

15. The interbody spinal implant of claim 13, wherein the body is comprised of a non-metal polymer, and the first integration plate and the optional second integration plate are comprised of a metal.

16. The interbody spinal implant of claim 13, wherein the body is comprised of a composite of a metal and a non-metal polymer selected from the group consisting of polyetheretherketone, hedrocel, and ultra-high molecular weight polyethylene, and the first integration plate and the optional second integration plate are comprised of a metal.

17. The interbody spinal implant of claim 13, further comprising bone graft material disposed in the substantially hollow center of the body, in the vertical aperture of the first integration plate, and in the vertical aperture of the second integration plate, and adapted to facilitate the formation of a solid fusion column within the spine.

18. The interbody spinal implant of claim 17, wherein the bone graft material is cancellous autograft bone, allograft bone, demineralized bone matrix (DBM), porous synthetic bone graft substitute, bone morphogenic protein (BMP), or a combination thereof.

19. The interbody spinal implant of claim 13, wherein the anterior portion width of the rim on the top surface of the first integration plate is less than the posterior portion width of the rim on the top surface of the first integration plate, and the anterior portion width of the rim on the top surface of the second integration plate is less than the posterior portion width of the rim on the top surface of the second integration plate.

20. The interbody spinal implant of claim 13, wherein the posterior portion width of the rim on the top surface of the first integration plate is less than the anterior portion width of the rim on the top surface of the first integration plate, and the posterior portion width of the rim on the top surface of the second integration plate is less than the anterior portion width of the rim on the top surface of the second integration plate.

21. The interbody spinal implant of claim 13, wherein the first lateral side width of the rim on the top surface of the first integration plate is less than the second lateral side width of the rim on the top surface of the first integration plate, and wherein the first lateral side width of the rim on the top surface of the second integration plate is less than the second lateral side width of the rim on the top surface of the second integration plate.

22. The interbody spinal implant of claim 13, wherein the maximum width at the center of the vertical aperture of the first integration plate ranges from about 50% to about 65% of the distance between the opposing lateral sides of the first integration plate, and wherein the maximum width at the center of the vertical aperture of the second integration plate ranges from about 50% to about 65% of the distance between the opposing lateral sides of the second integration plate.

23. The interbody spinal implant of claim 13, further comprising a lordotic angle adapted to facilitate alignment of the spine.

* * * * *